US012595261B2

(12) United States Patent
Zhao et al.

(10) Patent No.: US 12,595,261 B2
(45) Date of Patent: Apr. 7, 2026

(54) P2X3 AND/OR P2X2/3 RECEPTOR ANTAGONIST, PHARMACEUTICAL COMPOSITION CONTAINING SAME, AND USE THEREOF

(71) Applicant: BEIJING TIDE PHARMACEUTICAL CO., LTD., Beijing (CN)

(72) Inventors: Yanping Zhao, Beijing (CN); Hongjun Wang, Beijing (CN); Yeming Wang, Beijing (CN); Liying Zhou, Beijing (CN); Yanan Liu, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 1051 days.

(21) Appl. No.: 17/616,236

(22) PCT Filed: Jun. 5, 2020

(86) PCT No.: PCT/CN2020/094494
§ 371 (c)(1),
(2) Date: Dec. 3, 2021

(87) PCT Pub. No.: WO2020/244607
PCT Pub. Date: Dec. 10, 2020

(65) Prior Publication Data

US 2022/0332714 A1 Oct. 20, 2022

(30) Foreign Application Priority Data

Jun. 6, 2019 (CN) ......................... 201910494702.2

(51) Int. Cl.

| | |
|---|---|
| ***C07D 471/04*** | (2006.01) |
| ***C07D 491/048*** | (2006.01) |
| ***C07D 495/04*** | (2006.01) |
| ***C07D 498/04*** | (2006.01) |
| ***C07D 513/04*** | (2006.01) |

(52) U.S. Cl.
CPC ....... *C07D 471/04* (2013.01); *C07D 491/048* (2013.01); *C07D 495/04* (2013.01); *C07D 498/04* (2013.01); *C07D 513/04* (2013.01)

(58) Field of Classification Search
CPC .............. C07D 471/04; C07D 491/048; C07D 495/04; C07D 498/04; C07D 513/04; A61P 29/00; A61P 11/00; A61K 31/506
See application file for complete search history.

(56) References Cited

U.S. PATENT DOCUMENTS

2004/0162303 A1 8/2004 Bartkovitz et al.
2007/0049610 A1 * 3/2007 Dillon ..................... A61P 17/02 514/269

FOREIGN PATENT DOCUMENTS

| | | | | |
|---|---|---|---|---|
| EP | 0051879 | * | 5/1982 | ........... A61K 31/505 |
| EP | 0092614 A1 | * | 11/1983 | ............... B01D 3/22 |
| EP | 0 096 214 | | 12/1983 | |
| EP | 0441475 A2 | * | 8/1991 | ........... A61K 31/505 |
| JP | S57114581 | | 7/1982 | |
| JP | S58208277 | | 12/1983 | |
| JP | 2006-523183 | | 10/2006 | |
| JP | 2009-506998 | | 2/2009 | |
| JP | 2009-516666 | | 4/2009 | |
| JP | 2011-252004 | | 12/2011 | |
| JP | 2019-508445 | | 3/2019 | |
| KR | 10-2008-0041288 | | 5/2008 | |
| WO | 02/10156 | | 2/2002 | |
| WO | WO-0210156 A1 | * | 2/2002 | ........... C07D 307/86 |
| WO | 2004/069139 | | 8/2004 | |
| WO | 2005095359 | | 10/2005 | |
| WO | 2007025900 | | 3/2007 | |
| WO | 2007025925 | | 3/2007 | |
| WO | 2007/060110 | | 5/2007 | |
| WO | 2017160569 | | 9/2017 | |
| WO | 2017165255 | | 9/2017 | |
| WO | 2019085916 | | 5/2019 | |

OTHER PUBLICATIONS

Stella, J. Pharmaceutical Sciences, 2010, 99(12), pp. 4755-4765). (Year: 2010).*
Prescott John F.: "Sulfonamides, Diaminopyrimidines, and Their Combinations" In: "Antimicrobial Therapy in Veterinary Medicine", Aug. 16, 2013 (Aug. 16, 2013), Wiley, XP093041610, ISBN: 978-1-118-67501-4, pp. 279-294, DOI: 10.1002/9781118675014.ch17, Retrieved from the Internet: URL:https://onlinelibrary.wiley.com/doi/pdf/10.1002/9781118675014.ch17.
Han Xiaoya et al: "Broad-spectrum monoclonal antibody and a sensitive multi-residue indirect competitive enzyme-linked immunosorbent assay for the antibacterial synergists in samples of animal origin", Food Chemistry, vol. 280, May 1, 2019 (May 1, 2019), pp. 20-26, XP093041618, NL ISSN: 0308-8146, DOI: 10.1016/j.foodchem.2018.12.040.
Falco E A et al: "2,4-Diaminopyrimidines as Antimalarials", Journal of the American Chemical Society, American Chemical Society, vol. 73, No. 8, Aug. 1, 1951 (Aug. 1, 1951), pp. 3753-37587, XP002063219, ISSN: 0002-7863, DOI: 10.1021/JA01152A058.

(Continued)

*Primary Examiner* — Susanna Moore
*Assistant Examiner* — Luisalberto Gonzalez
(74) *Attorney, Agent, or Firm* — Robin L. Teskin; Baker, Donelson, Bearman, Caldwell & Berkowitz PC

(57) ABSTRACT

Disclosed are a P2X3 and/or P2X2/3 receptor antagonist of formula (I), a pharmaceutical composition containing same, and the use thereof for preventing or treating a disease regulated by the P2X3 and/or P2X2/3 receptor antagonist.

Formula (I)

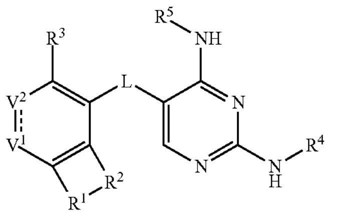

6 Claims, No Drawings

(56) References Cited

OTHER PUBLICATIONS

Alexander Stuart et al: "2,4-Diamino-5-benzylpyrimidineasn d Analogues as Antibacterial Agents. 6. A One-Step Synthesis of New Trimethoprim Derivatives and Activity Analysis by Molecular Modeling", Journal of Medicinal Chemistry, American Chemical Society, US, vol. 26, No. 5, Jan. 1, 1983 (Jan. 1, 1983), pp. 667-673, XP007906024, ISSN: 0022-2623, DOI: 10.1021/JM00359A009.

Ballini et al. "Characterization of three diaminopyrimidines as potent and selective antagonists of P2X3 and P2X2/3 receptors with in vivo efficacy in a pain model." British journal of pharmacology. Jul. 2011;163(6):1315-25.

* cited by examiner

P2X3 AND/OR P2X2/3 RECEPTOR ANTAGONIST, PHARMACEUTICAL COMPOSITION CONTAINING SAME, AND USE THEREOF

CROSS-REFERENCE TO RELATED APPLICATIONS

This application is a U.S. National Phase application of Int'l Appl. No. PCT/CN2020/094494, filed Jun. 5, 2020, which claims priority to Int'l Chinese Appl. No. 201910494702.2, filed Jun. 6, 2019, each of which are incorporated herein by reference in their entireties.

FIELD OF THE INVENTION

The present invention relates to a P2X3 and/or P2X2/3 receptor antagonist, a pharmaceutical composition comprising the same, and use thereof for the prophylaxis or treatment of a disease mediated by the P2X3 and/or P2X2/3 receptor antagonist.

BACKGROUND OF THE INVENTION

Purine compounds, acting via cell surface purinoceptors, have been implicated as having a variety of physiological and pathological roles. ATP, and to a lesser extent, adenosine, can stimulate sensory nerve endings resulting in intense pain and a pronounced increase in sensory nerve discharge. ATP receptors have been classified into two major families, the P2Y- and P2X-purinoreceptors, on the basis of the molecular structure, transduction mechanisms, and pharmacological characterization. The P2Y-purinoceptors are G-protein coupled receptors, while the P2X-purinoceptors are a family of ATP-gated cation channels. Purinoceptors, in particular, P2X receptors, can form homomultimers or heteromultimers. To date, cDNAs for multiple P2X receptor subtypes (including six homologous receptors: P2X1, P2X2, P2X3, P2X4, P2X5 and P2X7; and three heterologous receptors: P2X2/3, P2X4/6 and P2X1/5) have been cloned. The structure and chromosomal mapping of mouse genomic P2X3 receptor subunits have also been reported.

Studies have shown that P2X3 and/or P2X2/3 receptor antagonists can be used to treat diseases such as pain, etc. The present invention provides compounds as P2X receptor modulators, particularly P2X3 and/or P2X2/3 receptor antagonists.

SUMMARY OF THE INVENTION

The present invention provides a compound for use as a P2X receptor modulator (particularly P2X3 and/or P2X2/3 receptor antagonist), it effectively antagonize the P2X receptor (particularly P2X3 and/or P2X2/3 receptor), and has better physicochemical properties (e.g., solubility, physical and/or chemical stability), improved pharmacokinetic properties (e.g., improved bioavailability, proper half-life and duration of action), improved safety (low toxicity and/or less side effects, wide therapeutic window), and the like.

An aspect of the present invention provides a compound or a pharmaceutically acceptable salt, ester, stereoisomer, polymorph, solvate, N-oxide, isotopically labeled compound, metabolite or prodrug thereof, wherein the compound has the structure of Formula (I):

Formula (I)

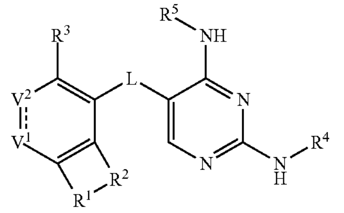

wherein:

L is selected from the group consisting of C(═O), CRR', NR, O, S, S═O and $S(═O)_2$, preferably $CH_2$, NH, O or S, and more preferably O;

$V^1$ is selected from the group consisting of $CR^{3'}$, N and NR (preferably NH);

$V^2$ is selected from the group consisting of $CR^6$ and C(═O);

---- represents either a single or a double bond, provided that when ---- is a single bond, $V^1$ is NR and $V^2$ is C(═O);

$R^1$ and $R^2$ are each independently selected from the group consisting of O, S, NR, $(CRR')_m$, $(CR═CR')_n$, $(C═O)_n$, C(═O)CRR', CRR'C(═O), C(═O)O, OC(═O), N═CR and CR═N;

m, at each occurrence, is each independently 1, 2, 3, 4 or 5;

n, at each occurrence, is each independently 1, 2, 3 or 4;

R and R', at each occurrence, are each independently selected from the group consisting of H, SEM, halogen, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl and $C_{6-12}$ aralkyl, and at most 2 ring members in the cyclic hydrocarbyl and heterocyclyl are C(═O);

$R^3$, $R^{3'}$ and $R^6$ are each independently selected from the group consisting of H, halogen, —CN, —$NH_2$, —OH, —SH, —Se—R, —$Si(R)_3$, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl, $C_{6-12}$ aralkyl, $C_{1-6}$ haloalkyl, —C(═O)$R^a$, —OC(═O)$R^a$, —C(═O)O$R^a$, —O$R^a$, —S$R^a$, —S(═O)$R^a$, —$S(═O)_2R^a$, —$S(═O)_2NR^aR^b$, —S(═O)(═NR)$R^a$, —$NR^aR^b$, —C(═O)$NR^aR^b$, —C(═S)$NR^aR^b$, —C(═NR)$NR^aR^b$, —$NR^a$—C(═O)$R^b$, —$NR^a$—C(═O)O$R^b$, —$NR^a$—$S(═O)_2$—$R^b$, —$NR^a$—C(═O)—$NR^aR^b$, —$C_{1-6}$ alkylene-$NR^aR^b$, —$C_{1-6}$ alkylene-O$R^a$, —$C_{1-6}$ alkylene-C(═O)R, —$C_{1-6}$ alkenylene-O$R^a$, —O—$C_{1-6}$ alkylene-$NR^aR^b$ and —P(═O)$R^aR^b$;

$R^4$ and $R^5$ are each independently selected from the group consisting of H, —C(═O)O$R^a$, —$NR^aR^b$, —$NR^a$—C(═O)$R^b$, —$NR^a$—C(═O)O$R^b$, —$C_{1-6}$ alkylene-$NR^aR^b$, —$C_{1-6}$ alkylene-O$R^a$, —$C_{1-6}$ alkylene-O—$C_{1-6}$ alkylene-O$R^a$, $C_{1-6}$ alkyl, $C_{1-6}$ haloalkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl and $C_{6-12}$ aralkyl;

the above alkyl, alkylene, alkenyl, alkynyl, cyclic hydrocarbyl, heterocyclyl, aryl, heteroaryl and aralkyl, at each occurrence, are each optionally substituted with one or more substituents independently selected from the group consisting of: halogen, hydroxyl, oxo, amino, cyano, nitro, —$Si(R)_3$, $C_{1-6}$ alkyl, saturated or partially unsaturated $C_{3-6}$ cyclic hydrocarbyl, saturated or partially unsaturated 3-10-membered heterocyclyl, $C_{6-10}$ aryl, 5-14-membered heteroaryl, $C_{6-12}$ aralkyl, —C(=O)$R^a$, —OC(=O)$R^a$, —C(=O)O$R^a$, —O$R^a$, —S$R^a$, —S(=O)$R^a$, —S(=O)$_2R^a$, —S(=O)$_2NR^aR^b$, —$NR^aR^b$, —C(=O)$NR^aR^b$, —$NR^a$—C(=O)$R^b$, —$NR^a$—C(=O)O$R^b$, —$NR^a$—S(=O)$_2$—$R^b$, —$NR^a$—C(=O)—$NR^aR^b$, —$C_{1-6}$ alkylene-$NR^aR^b$, —$C_{1-6}$ alkylene-O$R^a$, —$C_{1-6}$ alkenylene-O$R^a$ and —O—$C_{1-6}$ alkylene-$NR^aR^b$, the alkyl, cyclic hydrocarbyl, heterocyclyl, aryl, heteroaryl and aralkyl are further optionally substituted with one or more substituents independently selected from the group consisting of: halogen, hydroxyl, oxo, amino, cyano, nitro, —$NR^aR^b$, $C_{1-6}$ alkyl, —O—$C_{1-6}$ alkyl, saturated or partially unsaturated $C_{3-6}$ cyclic hydrocarbyl, saturated or partially unsaturated 3-10-membered heterocyclyl, $C_{6-10}$ aryl, 5-14-membered heteroaryl and $C_{6-12}$ aralkyl; and $R^a$ and $R^b$, at each occurrence, are each independently selected from the group consisting of H, —OH, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl and $C_{6-12}$ aralkyl; alternatively, $R^a$ and $R^b$ together with the atom to which they are attached form a 3-12-membered heterocycle or heteroaromatic ring, and the above groups are further optionally substituted with one or more substituents independently selected from the group consisting of: halogen, hydroxyl, oxo, amino, cyano, nitro, $C_{1-6}$ alkyl, —O—$C_{1-6}$ alkyl, saturated or partially unsaturated $C_{3-6}$ cyclic hydrocarbyl, saturated or partially unsaturated 3-10-membered heterocyclyl, $C_{6-10}$ aryl, 5-14-membered heteroaryl and $C_{6-12}$ aralkyl.

Another aspect of the present invention provides a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof, and one or more pharmaceutically acceptable carriers, and the pharmaceutical composition is preferably in the form of a solid, semi-solid, liquid, or gas preparation.

Another aspect of the present invention provides use of the compound of the present invention or a pharmaceutically acceptable salt, ester, stereoisomer, polymorph, solvate, N-oxide, isotopically labeled compound, metabolite or prodrug thereof or the pharmaceutical composition of the present invention in the manufacture of a medicament for the treatment of a disease mediated by the P2X3 and/or P2X2/3 receptor antagonist.

Another aspect of the present invention provides the compound of the present invention or a pharmaceutically acceptable salt, ester, stereoisomer, polymorph, solvate, N-oxide, isotopically labeled compound, metabolite or prodrug thereof or the pharmaceutical composition of the present invention for use in the treatment of a disease mediated by the P2X3 and/or P2X2/3 receptor antagonist.

Another aspect of the present invention provides a method for the prophylaxis or the treatment of a disease mediated by the P2X3 and/or P2X2/3 receptor antagonist, wherein the method comprises administering to a subject in need thereof an effective amount of the compound of the present invention or a pharmaceutically acceptable salt, ester, stereoisomer, polymorph, solvate, N-oxide, isotopically labeled compound, metabolite or prodrug thereof or the pharmaceutical composition of the present invention.

DETAILED DESCRIPTION OF THE INVENTION

Definition

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkylene" refers to a saturated divalent hydrocarbyl, preferably refers to a saturated divalent hydrocarbyl having 1, 2, 3, 4, 5 or 6 carbon atoms, e.g., methylene, ethylene, propylene or butylene.

As used herein, the term "alkyl" is defined as a linear or branched saturated aliphatic hydrocarbon. In some embodiments, alkyl has 1-12, e.g., 1-6, carbon atoms. For example, as used herein, the term "$C_{1-6}$ alkyl" refers to a linear or branched group having 1-6 carbon atoms (such as methyl, ethyl, n-propyl, isopropyl, n-butyl, isobutyl, sec-butyl, tert-butyl, n-pentyl, isopentyl, neopentyl, or n-hexyl), which is optionally substituted with one or more (e.g., 1 to 3) suitable substituents such as halogen (in which case the group may be referred to as "haloalkyl") (e.g., $CH_2F$, $CHF_2$, $CF_3$, $CCl_3$, $C_2F_5$, $C_2Cl_5$, $CH_2CF_3$, $CH_2Cl$ or —$CH_2CH_2CF_3$ etc.). The term "$C_{1-4}$ alkyl" refers to a linear or branched aliphatic hydrocarbon chain having 1-4 carbon atoms (i.e., methyl, ethyl, n-propyl, isopropyl, n-butyl, isobutyl, sec-butyl or tert-butyl).

As used herein, the term "alkenyl" refers to a linear or branched monovalent hydrocarbyl having a double bond and 2-6 carbon atoms ("$C_{2-6}$ alkenyl"). The alkenyl is e.g., vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl and 4-methyl-3-pentenyl. When the compound of the present invention contains an alkenyl group, the compound may exist as the pure E (entgegen) form, the pure Z (zusammen) form, or any mixture thereof.

As used herein, the term "alkynyl" refers to a monovalent hydrocarbyl containing one or more triple bond, and preferably having 2, 3, 4, 5 or 6 carbon atoms, e.g., ethynyl or propynyl.

As used herein, the term "cycloalkyl" refers to a saturated monocyclic or polycyclic (e.g., bicyclic) hydrocarbon ring (e.g., monocyclic, such as cyclopropyl, cyclobutyl, cyclopentyl, cyclohexyl, cycloheptyl, cyclooctyl, or cyclononyl, or bicyclic, including spiro, fused or bridged cyclic system (such as bicyclo[1.1.1]pentyl, bicyclo[2.2.1]heptyl, bicyclo[3.2.1]octyl or bicyclo[5.2.0] nonyl, or decahydronaphthalene etc.)), which is optionally substituted with one or more (e.g., 1 to 3) suitable substituents. The cycloalkyl has 3 to 15 carbon atoms. For example, the term "$C_{3-6}$ cycloalkyl"

refers to a saturated monocyclic or polycyclic (e.g., bicyclic) hydrocarbon ring having 3 to 6 ring forming carbon atoms (e.g., cyclopropyl, cyclobutyl, cyclopentyl, or cyclohexyl), which is optionally substituted with one or more (e.g., 1 to 3) suitable substituents, e.g., methyl substituted cyclopropyl.

As used herein, the terms "cyclic hydrocarbylene", "cyclic hydrocarbyl" and "hydrocarbon ring" refer to a saturated (i.e., "cycloalkylene" and "cycloalkyl") or unsaturated (i.e., having one or more double and/or triple bonds in the ring) monocyclic or polycyclic hydrocarbon ring having e.g., 3-10 (suitably having 3-8, and more suitably having 3-6) ring carbon atoms, including but not limited to cyclopropyl(ene) (ring), cyclobutyl(ene) (ring), cyclopentyl(ene) (ring), cyclohexyl(ene) (ring), cycloheptyl(ene) (ring), cyclooctyl(ene) (ring), cyclononyl(ene) (ring), cyclohexenyl (ene) (ring), and the like.

As used herein, the terms "heterocyclyl", "heterocyclylene" and "heterocycle" refer to a saturated (i.e., heterocycloalkyl) or partially unsaturated (i.e., having one or more double and/or triple bonds in the ring) cyclic group having e.g. 3-10 (suitably having 3-8, and more suitably having 3-6) ring atoms, wherein at least one ring atom is a heteroatom selected from the group consisting of N, O and S, and the remaining ring atoms are C. For example, "3- to 10-membered heterocyclyl(ene)" of "3- to 10-membered heterocycle" refers to saturated or partially unsaturated heterocyclyl(ene) or heterocycle having 2-9 (e.g., 2, 3, 4, 5, 6, 7, 8 or 9) ring carbon atoms and one or more (e.g., 1, 2, 3, or 4) heteroatoms independently selected from the group consisting of N, O and S. Examples of heterocyclylene, heterocyclyl and heterocycle include, but are not limited to oxiranyl (ene), aziridinyl(ene), azetidinyl(ene), oxetanyl(ene), tetrahydrofuranyl(ene), dioxolinyl(ene), pyrrolidinyl(ene), pyrrolidonyl(ene), imidazolidinyl(ene), pyrazolidinyl(ene), pyrrolinyl(ene), tetrahydropyranyl(ene), piperidinyl(ene), morpholinyl(ene), dithianyl(ene), thiomorpholinyl(ene), piperazinyl(ene) or trithianyl(ene). Said group also encompasses a bicyclic system, including a spiro, fused, or bridged system (e.g., 8-azaspiro[4.5]decane, 3,9-diazaspiro[5.5]undecane, 2-azabicyclo[2.2.2] octane, etc.). Heterocyclylene, heterocyclyl and heterocycle may optionally be substituted with one or more (e.g. 1, 2, 3 or 4) suitable substituents.

As used herein, the terms "aryl(ene)" and "aromatic ring" refer to an all-carbon monocyclic or fused-ring polycyclic aromatic group having a conjugated $\pi$ electron system. For example, as used herein, the terms "$C_{6-10}$ aryl(ene)" and "$C_{6-10}$ aromatic ring" refer to an aromatic group containing 6 to 10 carbon atoms, such as phenyl(ene) (benzene ring) or naphthyl(ene) (naphthalene ring). Aryl(ene) or aromatic ring is optionally substituted with one or more (such as 1 to 3) suitable substituents (e.g., halogen, —OH, —CN, —$NO_2$, and $C_{1-6}$ alkyl, etc.).

As used herein, the terms "heteroaryl(ene)" and "heteroaromatic ring" refer to a monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same to different. Moreover, in each case, it can be benzo-fused. In particular, "heteroaryl (ene)" or "heteroaromatic ring" is selected from the group consisting of thienyl(ene), furyl(ene), pyrrolyl(ene), oxazolyl(ene), thiazolyl(ene), imidazolyl(ene), pyrazolyl(ene), isoxazolyl(ene), isothiazolyl(ene), oxadiazolyl(ene), triazolyl(ene), thiadiazolyl(ene) etc., and benzo derivatives thereof; or pyridinyl(ene), pyridazinyl(ene), pyrimidinyl (ene), pyrazinyl(ene), triazinyl(ene), etc., and benzo derivatives thereof.

As used herein, the term "aralkyl" preferably means aryl or heteroaryl substituted alkyl, wherein aryl, heteroaryl and alkyl are as defined herein. Normally, the aryl group may have 6-14 carbon atoms, the heteroaryl group may have 5-14 ring atoms, and the alkyl group may have 1-6 carbon atoms. Exemplary aralkyl group includes, but is not limited to, benzyl, phenylethyl, phenylpropyl, phenylbutyl.

As used herein, the term "halo" or "halogen" are defined to include F, Cl, Br, or I.

As used herein, the term "nitrogen containing heterocycle" refers to a saturated or unsaturated monocyclic or bicyclic group having 2, 3, 4, 5, 6, 7, 8, 9, 10, 11, 12 or 13 carbon atoms and at least one nitrogen atom in the ring, which may further optionally comprise one or more (e.g., one, two, three or four) ring members selected from the group consisting of N, O, C═O, S, S═O and S(═O)$_2$. The nitrogen containing heterocycle is attached to the rest of the molecule through the nitrogen atom and any other ring atom in said nitrogen containing heterocycle. The nitrogen containing heterocycle is optionally benzo-fused, and is preferably attached to the rest of the molecule through the nitrogen atom in said nitrogen containing heterocycle and any carbon atom in the fused benzene ring.

The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

If a substituent is described as being "optionally substituted", the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more from a list of substituents, one or more of the hydrogens on the nitrogen (to the extent there are any) may each be replaced with an independently selected optional substituent.

If substituents are described as being "independently selected" from a group, each substituent is selected independent of the other(s). Each substituent therefore may be identical to or different from the other substituent(s).

As used herein, the term "one or more" means one or more than one (e.g., 2, 3, 4, 5 or 10) as reasonable.

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable.

The present invention also includes all pharmaceutically acceptable isotopically labeled compounds, which are identical to those of the present invention except that one or more atoms are replaced by an atom having the same atomic number, but an atomic mass or mass number different from the atomic mass or mass number which predominates in nature. Examples of isotopes suitable for inclusion in the compound of the present invention include, but are not limited to, isotopes of hydrogen, such as $^{2}H$, $^{3}H$; carbon, such as $^{11}C$, $^{13}C$, and $^{14}C$; chlorine, such as $^{36}Cl$; fluorine, such as $^{18}F$; iodine, such as $^{123}I$ and $^{125}I$; nitrogen, such as $^{13}N$ and $^{15}N$; oxygen, such as $^{15}O$, $^{17}O$, and $^{18}O$; phosphorus, such as $^{32}P$; and sulfur, such as $^{35}S$. Certain isotopically labeled compounds of the present invention, for example those incorporating a radioactive isotope, are useful in drug and/or substrate tissue distribution studies (e.g., assays). The radioactive isotopes tritium, i.e., $^{3}H$, and carbon-14, i.e., $^{14}C$, are particularly useful for this purpose in view of their ease of incorporation and ready means of detection. Substitution with positron-emitting isotopes, such as $^{11}C$, $^{18}F$, $^{15}O$ and $^{13}N$, can be useful in positron emission tomography (PET) studies for examining substrate receptor occupancy. Isotopically labeled compounds of the present invention can generally be prepared by processes analogous to those described in the accompanying Schemes and/or in the Examples and Preparations, by using an appropriate isotopically labeled reagent in place of the non-labeled reagent previously employed. Pharmaceutically acceptable solvates in accordance with the invention include those wherein the solvent of crystallization may be isotopically substituted, e.g., $D_2O$, acetone-$d_6$, or DMSO-$d_6$.

The term "stereoisomer" refers to isomers with at least one asymmetric center. A compound having one or more (e.g., one, two, three or four) asymmetric centers can give rise to a racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

The chemical bonds of the compound of the present invention may be depicted herein using a solid line (), a solid wedge (), or a dotted wedge (). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Unless stated otherwise, it is intended that the compound of the present invention can exist as stereoisomers, which include cis and trans isomers, optical isomers such as R and S enantiomers, diastereomers, geometric isomers, rotational isomers, conformational isomers, atropisomers, and mixtures thereof. The compound of the present invention may exhibit more than one type of isomerism, and consist of mixtures thereof (such as racemates and diastereomeric pairs).

The present invention includes all possible crystalline forms or polymorphs of the compound of the present invention, either as a single polymorph, or as a mixture of more than one polymorphs, in any ratio.

It also should be understood that, certain compounds of the present invention can be used for the treatment in a free form, or where appropriate, in a form of a pharmaceutically acceptable derivative. In the present invention, the pharmaceutically acceptable derivative includes, but is not limited to a pharmaceutically acceptable salt, ester, solvate, N-oxide, metabolite or prodrug, which can directly or indirectly provide the compound of the present invention or a metabolite or residue thereof after being administered to a patient in need thereof. Therefore, "the compound of the present invention" mentioned herein also means to encompass various derivative forms of the compound as mentioned above.

A pharmaceutically acceptable salt of the compound of the present invention includes an acid addition salt and a base addition salt thereof.

A suitable acid addition salt is formed from an acid which forms a pharmaceutically acceptable salt. Specific examples include acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms a pharmaceutically acceptable salt. Specific examples include aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, 2002). The method for preparing a pharmaceutically acceptable salt of the compound of the present invention is known to a person skilled in the art.

As used herein, the term "ester" refers to those derived from the compounds of the various formulae in the present application, which include physiologically-hydrolyzable esters (which may be hydrolyzed under physiological conditions to release the compounds of the present invention in the form of free acids or alcohols). The compound of the present invention itself may be an ester as well.

The compound of the present invention can exist as a solvate (preferably a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

As can be appreciated by a person skilled in the art, not all nitrogen containing heterocycles can form N-oxides since the nitrogen requires an available lone-pair electron for oxidation to the oxide; a person skilled in the art will recognize those nitrogen containing heterocycles which can form N-oxides. A person skilled in the art will also recognize that tertiary amines can form N-oxides. Synthetic methods for the preparation of N-oxides of heterocycles and tertiary amines are well known to a person skilled in the art, and they include the oxidation of heterocycles and tertiary amines with peroxy acids such as peracetic acid and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in literatures, see e.g., T. L. Gilchrist, *Comprehensive Organic Synthesis*, vol. 7, pp 748-750; A. R. Katritzky and A. J. Boulton, Eds., Academic Press; and G. W. H. Cheeseman and E. S. G. Werstiuk,

*Advances in Heterocyclic Chemistry*, vol. 22, pp 390-392, A. R. Katritzky and A. J. Boulton, Eds., Academic Press.

The metabolite of the compound of the present invention, namely a substance formed in vivo upon administration of the compound of the present invention, is also included within the scope of the present invention. Such a product may result e.g., from the oxidation, reduction, hydrolysis, amidation, de-amidation, esterification, enzymolysis, and the like, of the administered compound. Accordingly, the present invention encompasses the metabolite of the compound of the present invention, including a compound produced by a method comprising contacting the compound of the present invention with a mammal for a period of time sufficient to result in a metabolic product thereof.

Also within the scope of the present invention is a prodrug of the compound of the invention, which is certain derivative of the compound of the invention that may have little or no pharmacological activity itself, but can, when administered into or onto the body, be converted into the compound of the invention having the desired activity, for example, by hydrolytic cleavage. In general, such prodrug will be a functional derivative of the compound which is readily converted in vivo into the compound with desired therapeutic activity. Further information on the use of the prodrug may be found in "Pro-drugs as Novel Delivery Systems", Vol. 14, ACS Symposium Series (T. Higuchi and V. Stella). The prodrug in accordance with the invention can, for example, be produced by replacing appropriate functionalities present in the compound of the present invention with certain moieties known to those skilled in the art as "pro-moieties" as described, for example, in "Design of Prodrugs" by H. Bundgaard (Elsevier, 1985).

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in T. W. Greene & P. G. M. Wuts, Protective Groups in Organic Synthesis, John Wiley & Sons, 1991, which is incorporated herein by reference. The protecting groups may be removed at a convenient subsequent stage using methods known from the art.

The term "about" refers to a range within ±10%, preferably within ±5%, and more preferably within ±2% of the specified value.

SPECIFIC EMBODIMENTS

Compound

In some embodiments, the present invention provides a compound or a pharmaceutically acceptable salt, ester, stereoisomer, polymorph, solvate, N-oxide, isotopically labeled compound, metabolite or prodrug thereof, wherein the compound has the structure of Formula (I):

Formula (I)

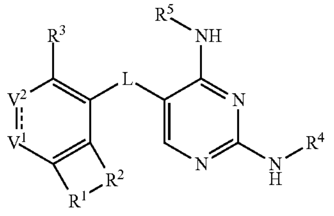

wherein:

L is selected from the group consisting of C(═O), CRR', NR, O, S, S═O and $S(═O)_2$, preferably $CH_2$, NH, O or S, and more preferably O;

$V^1$ is selected from the group consisting of $CR^{3'}$, N and NR (preferably NH);

$V^2$ is selected from the group consisting of $CR^6$ and C(═O);

---- represents either a single or a double bond, provided that when ---- is a single bond, $V^1$ is NR and $V^2$ is C(═O);

$R^1$ and $R^2$ are each independently selected from the group consisting of O, S, NR, $(CRR')_m$, $(CR═CR')_n$, $(C═O)_n$, C(═O)CRR', CRR'C(═O), C(═O)O, OC(═O), N═CR and CR═N;

m, at each occurrence, is each independently 1, 2, 3, 4 or 5;

n, at each occurrence, is each independently 1, 2, 3 or 4;

R and R', at each occurrence, are each independently selected from the group consisting of H, SEM, halogen, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl and $C_{6-12}$ aralkyl, and at most 2 ring members in the cyclic hydrocarbyl and heterocyclyl are C(═O);

$R^3$, $R^{3'}$ and $R^6$ are each independently selected from the group consisting of H, halogen, —CN, —$NH_2$, —OH, —SH, —Se—R, —$Si(R)_3$, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl, $C_{6-12}$ aralkyl, $C_{1-6}$ haloalkyl, —C(═O)$R^a$, —OC(═O)$R^a$, —C(═O)O$R^a$, —O$R^a$, —S$R^a$, —S(═O)$R^a$, —$S(═O)_2R^a$, —$S(═O)_2NR^aR^b$, —S(═O)(═NR)$R^a$, —$NR^aR^b$, —C(═O)$NR^aR^b$, —C(═S)$NR^aR^b$, —C(═NR)$NR^aR^b$, —$NR^a$—C(═O)$R^b$, —$NR^a$—C(═O)O$R^b$, —$NR^a$—$S(═O)_2$—$R^b$, —$NR^a$—C(═O)—$NR^aR^b$, —$C_{1-6}$ alkylene-$NR^aR^b$, —$C_{1-6}$ alkylene-O$R^a$, —$C_{1-6}$ alkylene-C(═O)R, —$C_{1-6}$ alkenylene-O$R^a$, —O—$C_{1-6}$ alkylene-$NR^aR^b$ and —P(═O)$R^aR^b$;

$R^4$ and $R^5$ are each independently selected from the group consisting of H, —C(═O)O$R^a$, —$NR^aR^b$, —$NR^a$—C(═O)$R^b$, —$NR^a$—C(═O)O$R^b$, —$C_{1-6}$ alkylene-$NR^aR^b$, —$C_{1-6}$ alkylene-O$R^a$, —$C_{1-6}$ alkylene-O—$C_{1-6}$ alkylene-O$R^a$, $C_{1-6}$ alkyl, $C_{1-6}$ haloalkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl and $C_{6-12}$ aralkyl;

the above alkyl, alkylene, alkenyl, alkynyl, cyclic hydrocarbyl, heterocyclyl, aryl, heteroaryl and aralkyl, at each occurrence, are each optionally substituted with one or more substituents independently selected from the group consisting of: halogen, hydroxyl, oxo, amino, cyano, nitro, —$Si(R)_3$, $C_{1-6}$ alkyl, saturated or partially unsaturated $C_{3-6}$ cyclic hydrocarbyl, saturated or partially unsaturated 3-10-membered heterocyclyl, $C_{6-10}$ aryl, 5-14-membered heteroaryl, $C_{6-12}$ aralkyl, —C(═O)$R^a$, —OC(═O)$R^a$, —C(═O)O$R^a$, —O$R^a$, —S$R^a$, —S(═O)$R^a$, —$S(═O)_2R^a$, —$S(═O)_2NR^aR^b$, —$NR^aR^b$, —C(═O)$NR^aR^b$, —$NR^a$—C(═O)$R^b$, —$NR^a$—C(═O)O$R^b$, —$NR^a$—$S(═O)_2$—$R^b$, —$NR^a$—C(═O)—$NR^aR^b$, —$C_{1-6}$ alkylene-$NR^aR^b$, —$C_{1-6}$ alkylene-O$R^a$, —$C_{1-6}$ alkenylene-O$R^a$ and —O—$C_{1-6}$ alkylene-$NR^aR^b$, the alkyl, cyclic hydrocarbyl, heterocyclyl, aryl, heteroaryl and aralkyl are further optionally substituted with one or more substituents independently selected from the group consisting of: halogen, hydroxyl, oxo, amino, cyano, nitro, —$NR^aR^b$, $C_{1-6}$ alkyl, —O—$C_{1-6}$ alkyl, saturated or partially unsaturated $C_{3-6}$ cyclic hydrocarbyl, saturated or partially unsaturated 3-10-membered heterocyclyl, $C_{6-10}$ aryl, 5-14-membered heteroaryl and $C_{6-12}$ aralkyl; and $R^a$ and $R^b$, at each occurrence, are each independently selected from the group consisting of H, —OH, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl and $C_{6-12}$ aralkyl; alternatively, $R^a$ and $R^b$ together with the atom to which they are attached form a 3-12-membered heterocycle or heteroaromatic ring, and the above groups are further optionally substituted with one or more substituents independently selected from the group consisting of: halogen, hydroxyl, oxo, amino, cyano, nitro, $C_{1-6}$ alkyl, —O—$C_{1-6}$ alkyl, saturated or partially unsaturated $C_{3-6}$ cyclic hydrocarbyl, saturated or partially unsaturated 3-10-membered heterocyclyl, $C_{6-10}$ aryl, 5-14-membered heteroaryl and $C_{6-12}$ aralkyl.

In some embodiments, R and R', at each occurrence, are each independently selected from the group consisting of H, SEM, F, Cl, Br, I, methyl, ethyl, n-propyl, isopropyl, n-butyl, isobutyl and tert-butyl; preferably, R and R', at each occurrence, are each independently selected from the group consisting of H, SEM, Cl and methyl.

In some embodiments, $R^1$ is selected from the group consisting of O, S, NR, $(CRR')_m$, $(CR{=}CR')_m$, N=CR and CR=N.

In preferred embodiments, $R^1$ is selected from the group consisting of O, S, NR, $(CR{=}CR')_n$, N=CR and CR=N.

In more preferred embodiments, $R^1$ is O, S, NH, $NCH_3$, N-SEM, N=CH, CH=N or CH=CH.

In most preferred embodiments, $R^1$ is O, S, NH or $NCH_3$.

In some embodiments, $R^2$ is selected from the group consisting of NR, $(CRR')_m$, $(CR{=}CR')_n$, $(C{=}O)_n$, C(=O)CRR', CRR'C(=O), C(=O)O, OC(=O), N=CR and CR=N; preferably, $R^2$ is selected from the group consisting of $(CRR')_n$, (CR=CR'), C(=O)CRR', N=CR and CR=N.

In preferred embodiments, $R^2$ is NH, $NCH_3$, N-SEM, $(CH_2)_2$, CH=CH, CCl=CH, CH=CCl, $C(CH_3){=}CH$, $CH{=}C(CH_3)$, $(C{=}O)_2$, $C(=O)CH_2$, $CH_2C(=O)$, C(=O)O, OC(=O), N=CH or CH=N.

In some embodiments, $R^a$ and $R^b$, at each occurrence, are each independently selected from the group consisting of H, —OH, methyl, ethyl, n-propyl, isopropyl, cyclopropyl, phenyl, benzyl, methoxy and ethoxy; alternatively, $R^a$ and $R^b$ together with the atom to which they are attached form a 5-8-membered heterocycle or heteroaromatic ring.

In some embodiments, $R^3$, $R^{3'}$ and $R^6$ are each independently selected from the group consisting of H, F, Cl, Br, I, —CN, —$NH_2$, —OH, —SH, —Se—$CH_3$, —$Si(CH_3)_3$, —$CH_2NH_2$, —$CH_2NHCH_3$, —$CH_2N(CH_3)_2$, methyl, ethyl, n-propyl, isopropyl, n-butyl, isobutyl, tert-butyl, cyclopropyl, cyclobutyl, cyclopentyl, cyclohexyl, vinyl, propenyl, allyl, ethynyl, propynyl, trifluoromethyl, acetyl, —C(=O)OH, —C(=O)$NH_2$, —C(=S)$NH_2$, —C(=NH)$NH_2$, —$NHCH_3$, —$NHCH_2CH_3$, —$NHCH_2CF_3$, —$N(CH_3)_2$, —$N(CH_3)(C_2H_5)$, —$N(C_2N_5)_2$, —$NHCH_2CH_2OH$, —NH—C(=O)$CH_3$, —NH—C(=O)CH=$CH_2$, methoxy, ethoxy, propoxy, phenyl, —NH—C(=O)—$NH_2$, —NH—C(=O)$OCH_3$, —$SCH_3$, —$SCH_2CH_3$, —$SC(CH_3)_3$, —SBn, —S(=O)$CH_3$, —S(=O)Bn, —$S(=O)_2CH_3$, —$S(—O)_2$Bn, —$S(=O)_2NH_2$, —$S(=O)_2NHCH_3$, —$S(=O)_2N(CH_3)_2$, —S(=O)(=NH)$CH_3$, —P(=O)$(CH_3)_2$, —P(=O)$(C_2H_5)_2$,

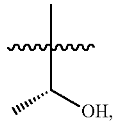,
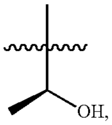,
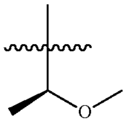,
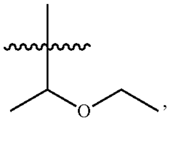,
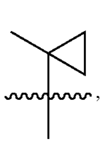,
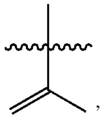,
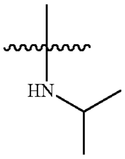,
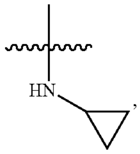,
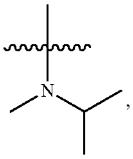,
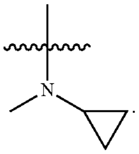.

In preferred embodiments, $R^3$ is isopropyl.

In preferred embodiments, $R^{3'}$ and $R^6$ are H.

In some embodiments, $R^4$ and $R^5$ are each independently selected from the group consisting of H, —C(=O)OC$(CH_3)_3$, —$NH_2$, —$NHCH_3$, —NHPh, —NHC(=O)$CH_3$, —NHBoc, methyl, ethyl, —$CH_2CF_3$, n-propyl, isopropyl, n-butyl, isobutyl, tert-butyl, cyclopropyl, cyclobutyl, cyclopentyl, cyclohexyl, phenyl, benzyl,

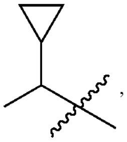,
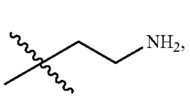,
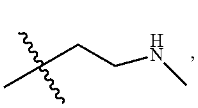,
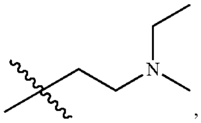,
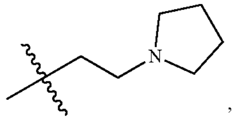,
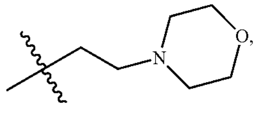,
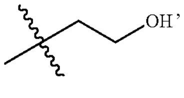'
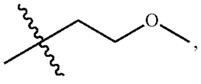,
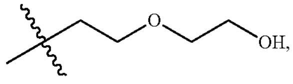,
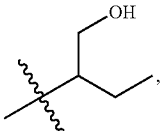,
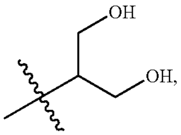, -continued
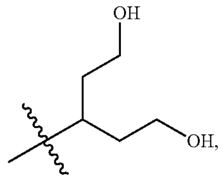
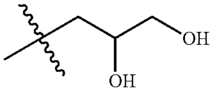
and
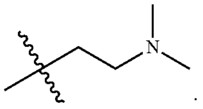
In preferred embodiments, $R^4$ and $R^5$ are H.
In some embodiments, the compound has the structure of any of the following formulae:
(II)
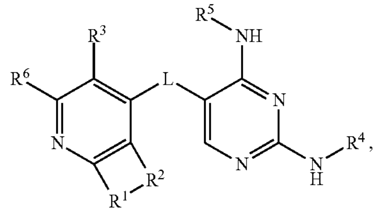
(III)
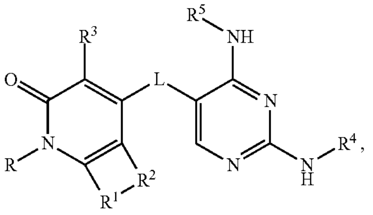
(IV)
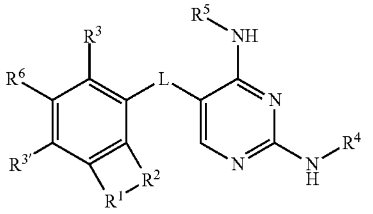
preferably, the Formula (II), (III) and (IV) respectively have the structure of any of the following formulae:
(II-1)
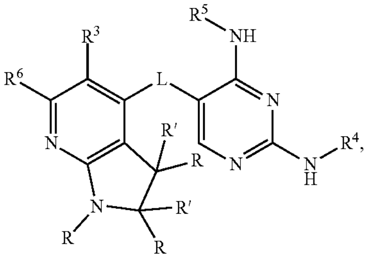
-continued
(III-1)
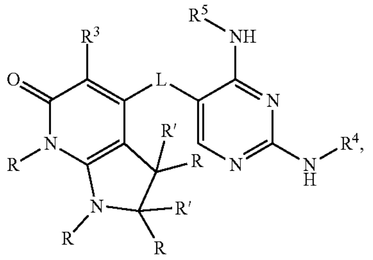
(IV-1)
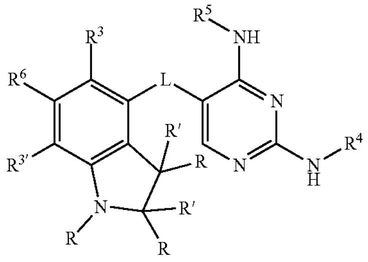
(II-2)
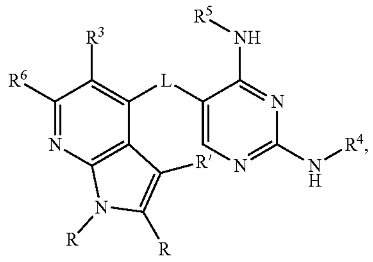
(III-2)
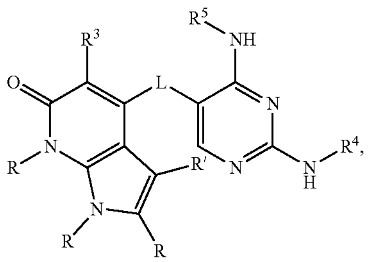
(IV-2)
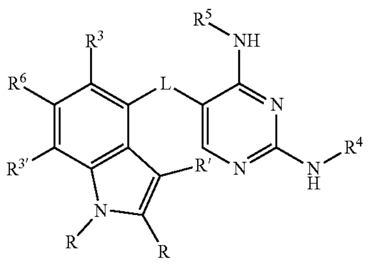
(II-3)
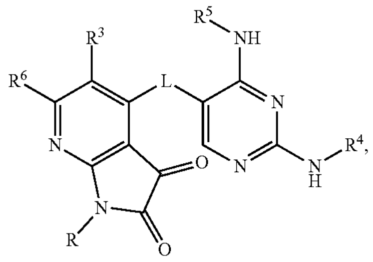

-continued
(III-3)
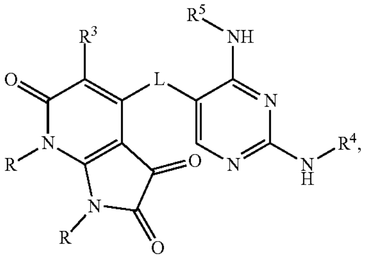
(IV-3)
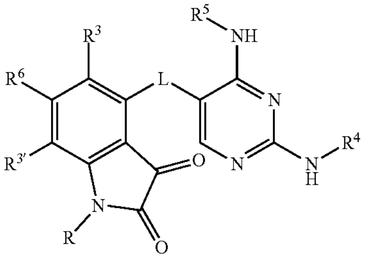
(II-4)
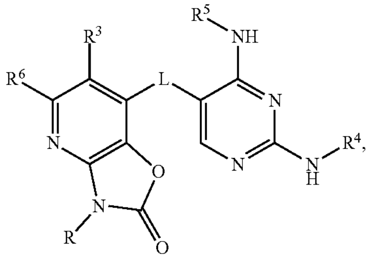
(III-4)
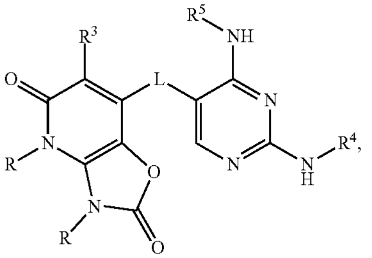
(IV-4)
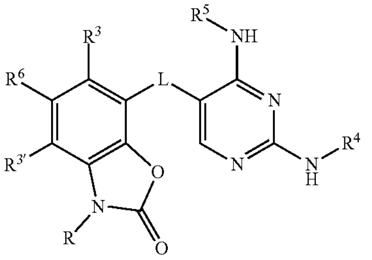
(II-5)
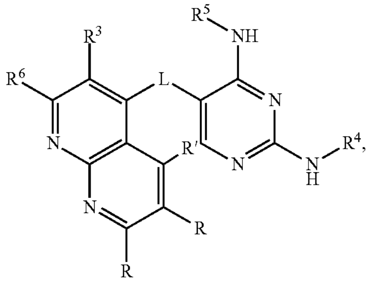
-continued
(III-5)
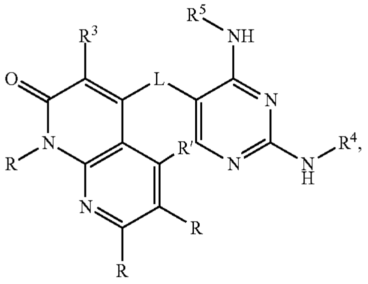
(IV-5)
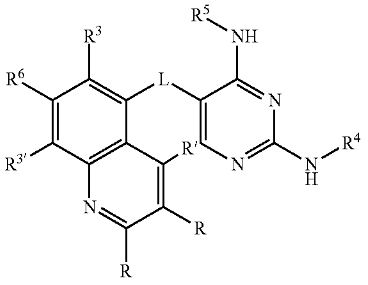
(II-5)
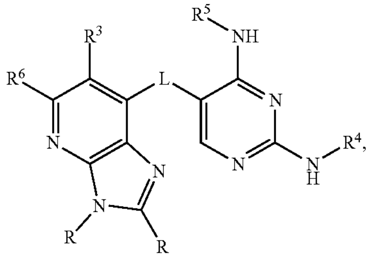
(III-6)
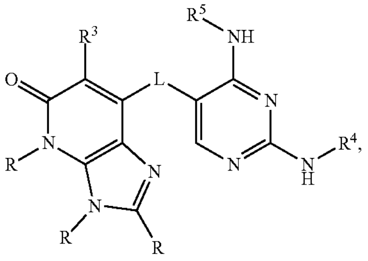
(IV-6)
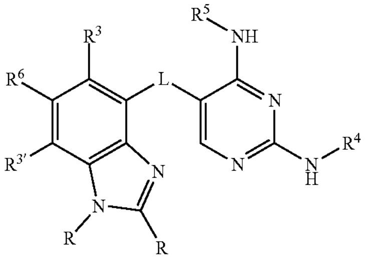
(II-7)
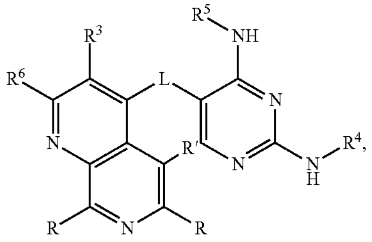

-continued
(III-7)
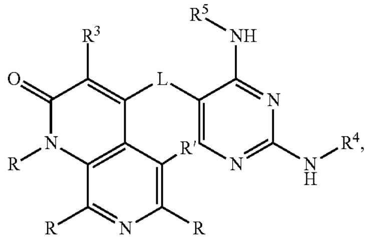
(IV-7)
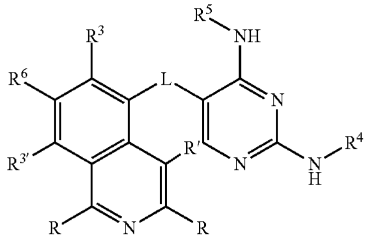
(II-8)
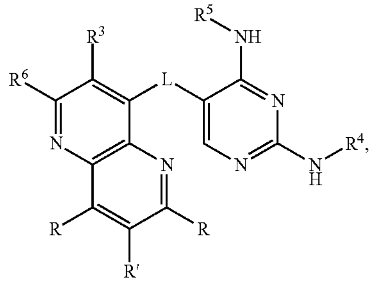
(III-8)
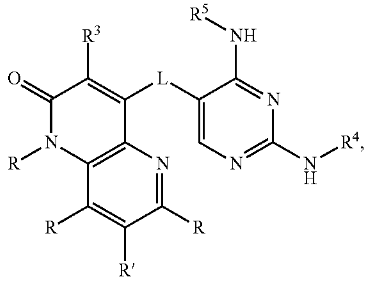
(IV-8)
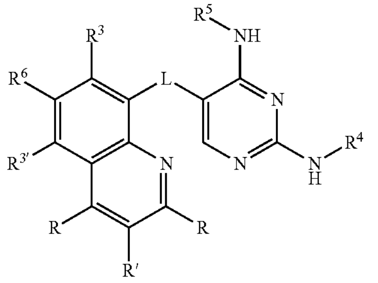
(II-9)
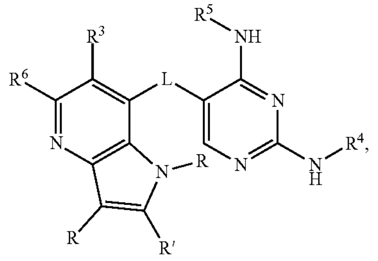
-continued
(III-9)
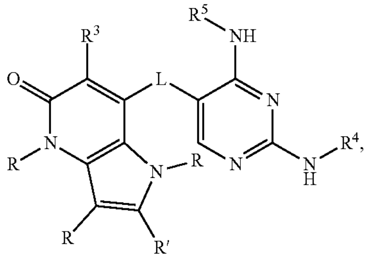
(IV-9)
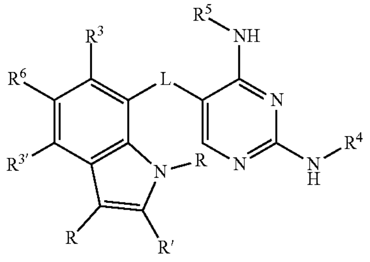
(II-10)
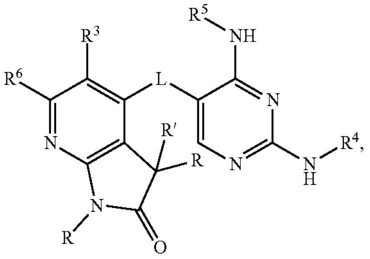
(III-10)
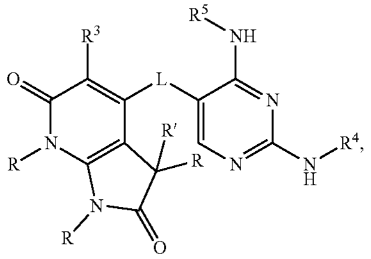
(IV-10)
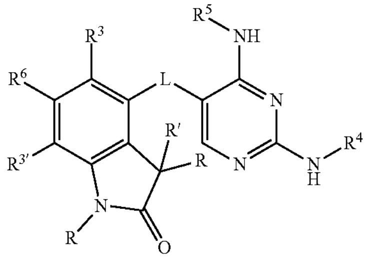
(II-11)
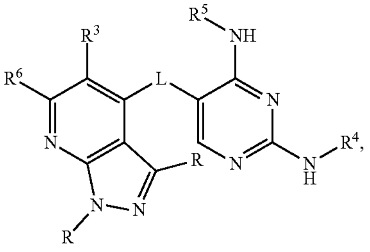

-continued
(III-11)
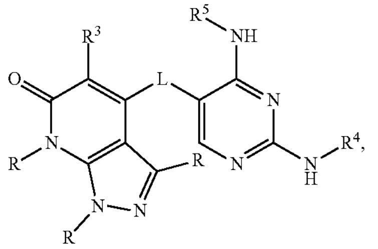
(IV-11)
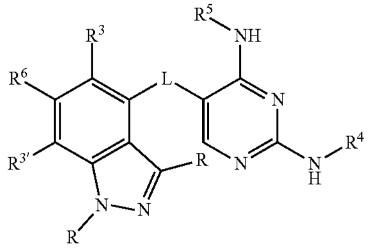
(II-12)
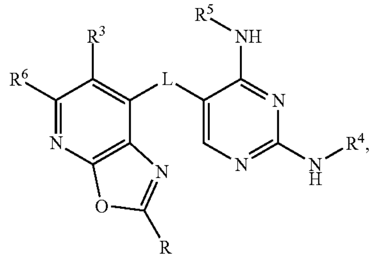
(III-12)
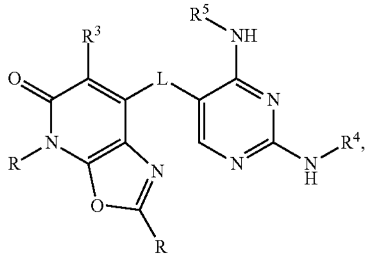
(IV-12)
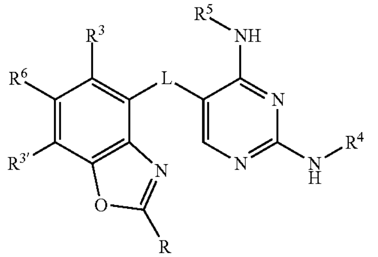
(II-13)
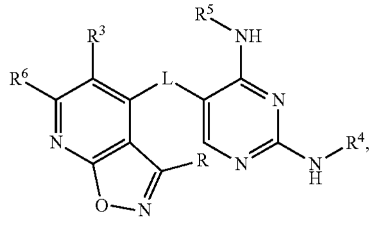
-continued
(III-13)
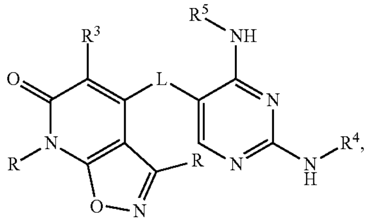
(IV-13)
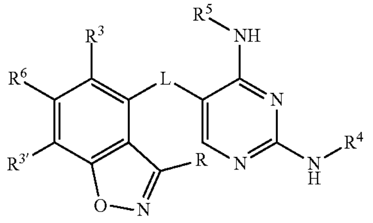
(II-14)
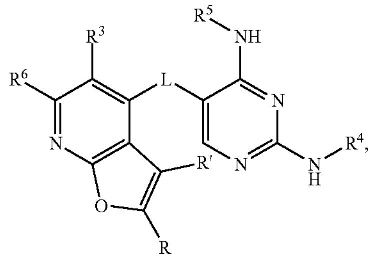
(III-14)
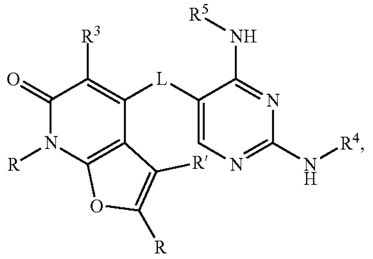
(IV-14)
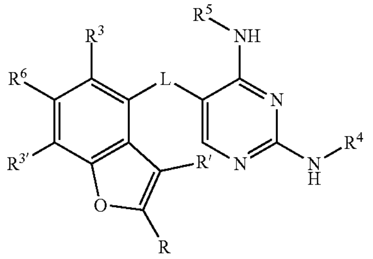
(II-15)
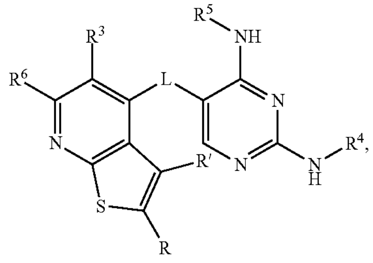

-continued (III-15)

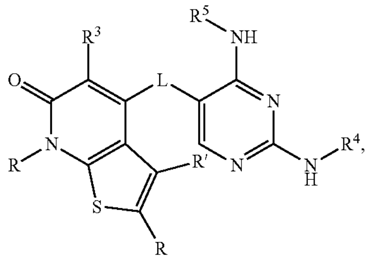

(IV-15)

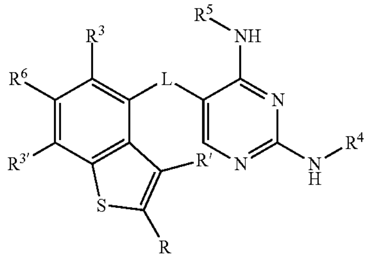

(II-16)

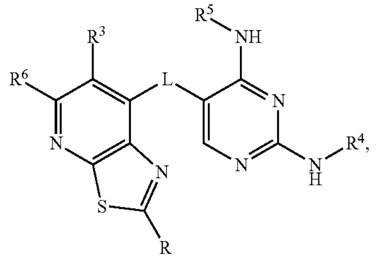

(III-16)

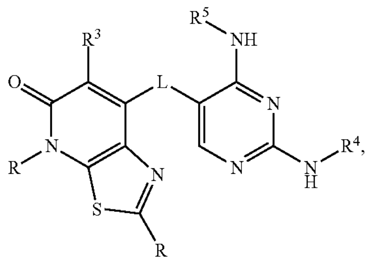

(IV-16)

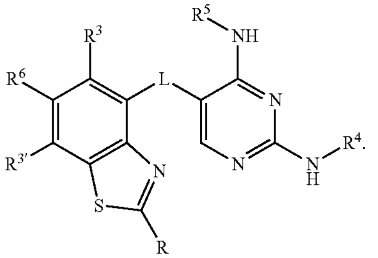

In preferred embodiments, the compound has the structure of Formula (V):

Formula (V)

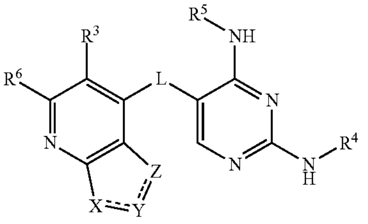

wherein:

- ---- represents either a single or a double bond, and the adjacent bonds are not double bonds simultaneously;
- L is selected from the group consisting of C(═O), CRR', NR, O, S, S═O and $S(═O)_2$, preferably $CH_2$, NH, O or S, and more preferably O; and
- X, Y and Z are each independently selected from the group consisting of CRR', CR, CR', N, NR, O, S and C(═O); wherein CRR', NR, O, S and C(═O) are attached to two single bonds, CR, CR' and N are attached to one single bond and one double bond;
- preferably, X, Y and Z are each independently selected from the group consisting of $CH_2$, CH, $C(CH_3)$, CCl, N, NH, $NCH_3$, N-SEM, O, S and C(═O), wherein $CH_2$, NH, $NCH_3$, N-SEM, O, S and C(═O) are attached to two single bonds, CH, $C(CH_3)$, CCl and N are attached to one single bond and one double bond;
- preferably, the Formula (V) has the structure of any of the following formulae:

(V-1)

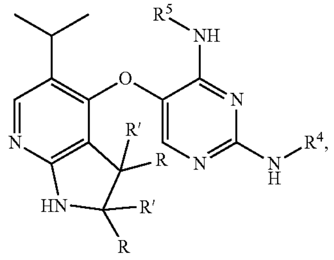

(V-2)

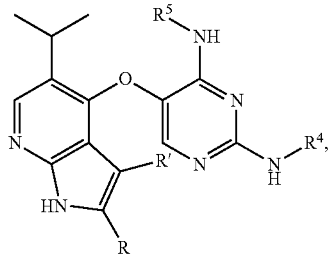

(V-3)

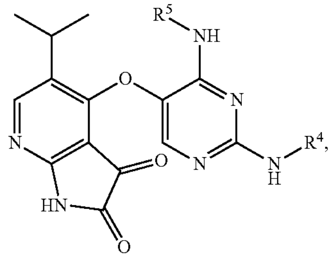

-continued
(V-4)
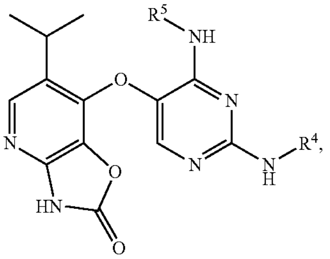
(V-5)
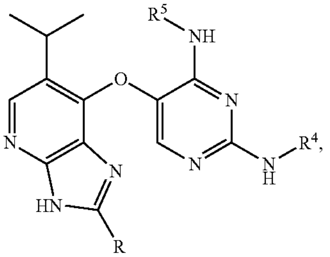
(V-6)
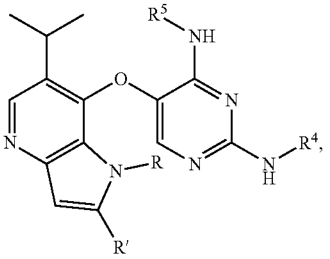
(V-7)
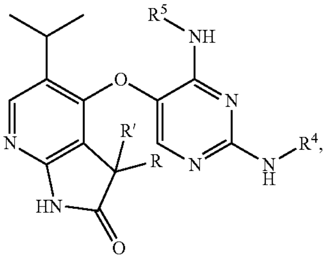
(V-8)
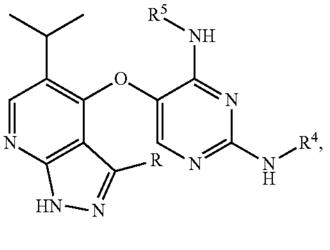
(V-9)
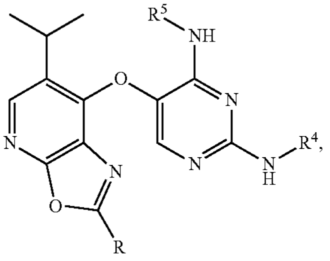
-continued
(V-10)
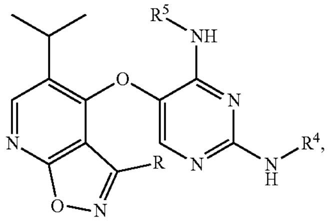
(V-11)
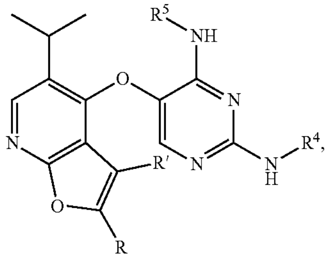
(V-12)
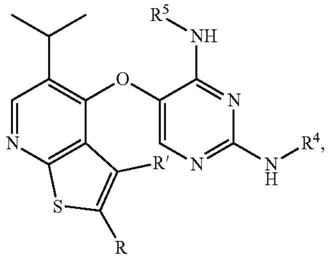
(V-13)
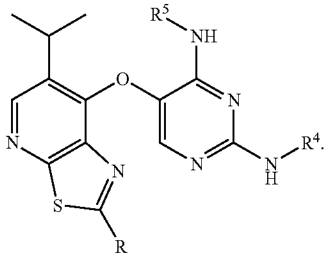
The compound obtained by any combination of the various embodiments is encompassed by the invention.
In preferred embodiments, the compound has the following structure:
C1
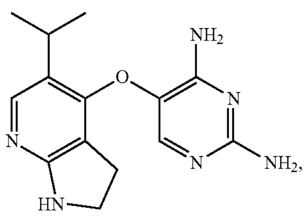
C2
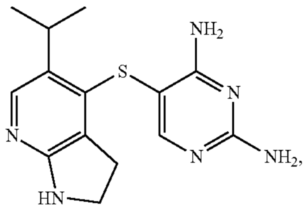

-continued
C3
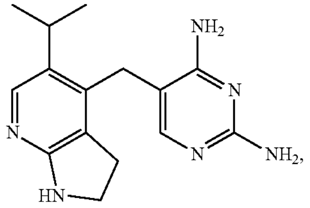
C4
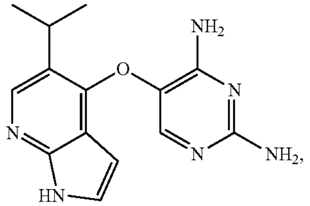
C5
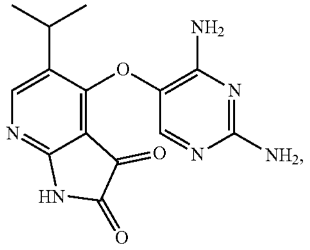
C6
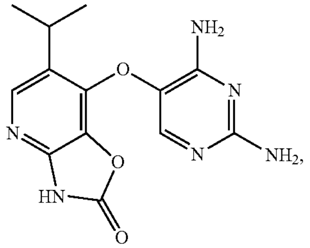
C7
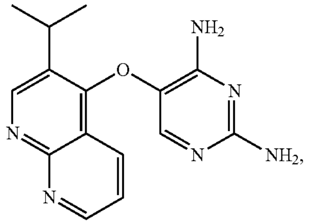
C8
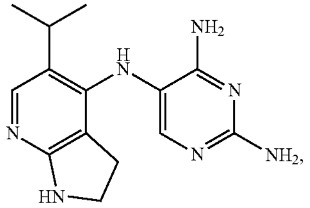
C9
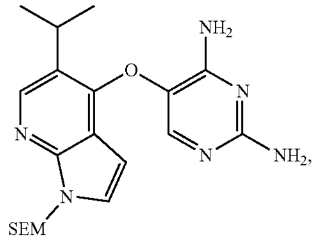
-continued
C10
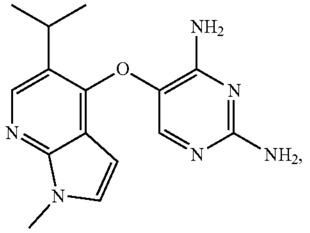
C11
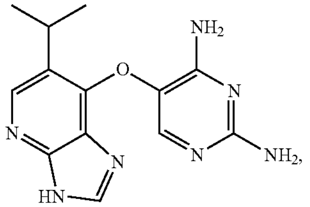
C12
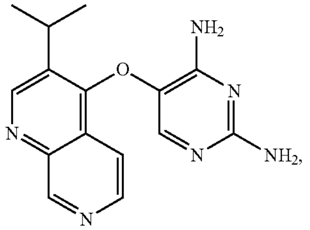
C13
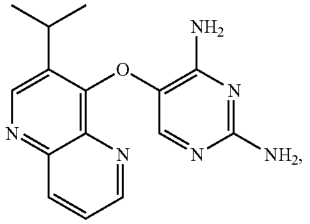
C14
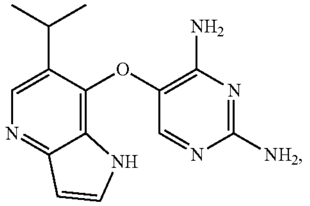
C15
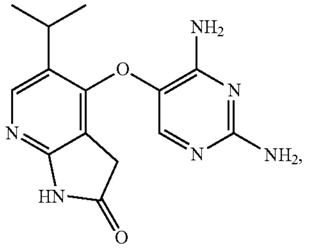

-continued

C16

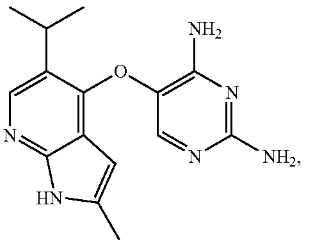

C17

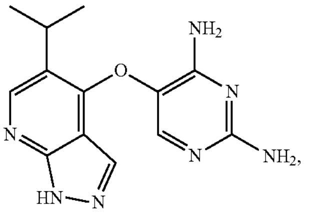

C18

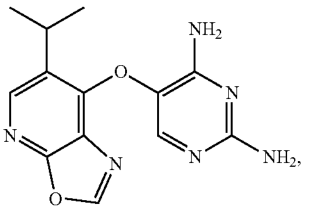

C19

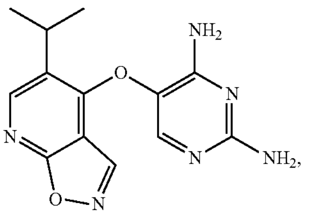

C20

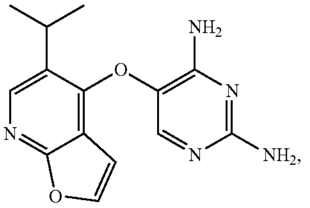

C21

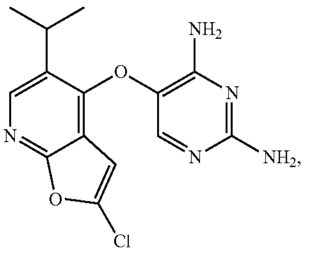

C22

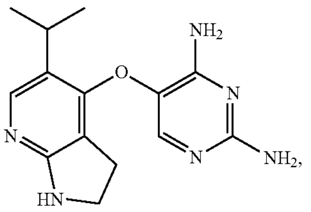

-continued

C23

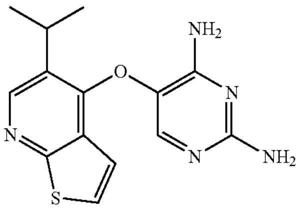

or

C24

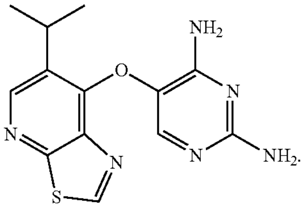

Pharmaceutical Composition and Therapeutic Method

In some embodiments, the present invention provides a pharmaceutical composition comprising a prophylactically or therapeutically effective amount of the compound of the present invention or a pharmaceutically acceptable salt, ester, stereoisomer, polymorph, solvate, N-oxide, isotopically labeled compound, metabolite or prodrug thereof and one or more pharmaceutically acceptable carriers, and the pharmaceutical composition is preferably in the form of a solid, semi-solid, liquid, or gas preparation. In some embodiments, the pharmaceutical composition can further comprise one or more additional therapeutic agents.

In some embodiments, the present invention provides use of the compound of the present invention or a pharmaceutically acceptable salt, ester, stereoisomer, polymorph, solvate, N-oxide, isotopically labeled compound, metabolite or prodrug thereof or the pharmaceutical composition of the present invention in the manufacture of a medicament for the treatment of a disease mediated by the P2X3 and/or P2X2/3 receptor antagonist.

In some embodiments, the present invention provides the compound of the present invention or a pharmaceutically acceptable salt, ester, stereoisomer, polymorph, solvate, N-oxide, isotopically labeled compound, metabolite or prodrug thereof or the pharmaceutical composition of the present invention for use in the treatment of a disease mediated by the P2X3 and/or P2X2/3 receptor antagonist.

In some embodiments, the present invention provides a method for the prophylaxis or the treatment of a disease mediated by the P2X3 and/or P2X2/3 receptor antagonist, wherein the method comprises administering to a subject in need thereof an effective amount of the compound of the present invention or a pharmaceutically acceptable salt, ester, stereoisomer, polymorph, solvate, N-oxide, isotopically labeled compound, metabolite or prodrug thereof or the pharmaceutical composition of the present invention.

In some embodiments, the disease mediated by the P2X3 and/or P2X2/3 receptor antagonist is selected from the group consisting of a urinary tract disease selected from reduced bladder capacity, frequent micturition, urge incontinence, stress incontinence, bladder hyperreactivity, benign prostatic hypertrophy, prostatitis, detrusor hyperreflexia, nocturia, urinary urgency, pelvic hypersensitivity, urethritis, pelvic pain syndrome, prostatodynia, cystitis, and idiopathic bladder hypersensitivity; pain disease selected from inflammatory pain, surgical pain, visceral pain, dental pain, premenstrual pain, central pain, pain due to burns, migraine and cluster headaches, nerve injury, neuritis, neuralgia, poisoning, ischemic injury, interstitial cystitis, cancer pain, viral, parasitic or bacterial infection, post-traumatic injury and pain associated with irritable bowel syndrome; cardiovascular system disease, preferably hypertension; respiratory disease selected from chronic obstructive pulmonary disease, asthma and bronchospasm; gastrointestinal disease selected from irritable bowel syndrome (preferably diarrhea-dominant irritable bowel syndrome), inflammatory bowel disease, biliary colic, renal colic, and pain associated with gastrointestinal distension.

The term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g. Remington's Pharmaceutical Sciences (1990).

The pharmaceutical composition of the present invention can act systemically and/or topically. To this end, it can be administered through a suitable route, such as through injection, (intravenous, intraarterial, subcutaneous, intraperitoneal, intramuscular injection, including dripping), or transdermal administration, or administered via oral, buccal, nasal, transmucosal, topical, as an ophthalmic formulation, or via inhalation For these routes of administration, the pharmaceutical composition of the present invention can be administered in a suitable dosage form.

Such dosage forms include, but are not limited to tablets, capsules, lozenges, hard candies, powders, sprays, creams, salves, suppositories, gels, pastes, lotions, ointments, aqueous suspensions, injectable solutions, elixirs, and syrups.

As used herein, the term "effective amount" refers to the amount of a compound being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, 25 mg, etc.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

In some embodiments, the pharmaceutical composition of the present invention can further comprise one or more additional therapeutic agents or prophylactic agents.

EXAMPLES

The present invention is further described with reference to the following examples, which are not provided to limit the scope of the present invention.

The structure of the compound was confirmed by nuclear magnetic resonance spectrum ($^1$H NMR) and/or mass spectrum (MS).

Chemical shifts (δ) are expressed in parts per million (ppm). $^1$H NMR was recorded on a Bruker 400 or Varian 300 spectrometer, the test solvent was deuterated methanol ($CD_3OD$), deuterated chloroform ($CDCl_3$) or hexadeuterated dimethyl sulfoxide (DMSO-$d_6$), and the internal standard was tetramethylsilane (TMS).

The LC-MS assay was conducted on Agilent LC-MS-1110 liquid chromatography-mass spectrometer, Agilent LC-MS-6110 liquid chromatography-mass spectrometer, Agilent LC-MS-6120 liquid chromatography-mass spectrometer (Manufacturer: Agilent) or Shimadzu LC-MS-2020.

Preparative high-performance liquid chromatography was conducted on MS induced AutoPurification system (Waters), Gilson GX-281 (Gilson), or semi-preparative liquid chromatograph (Tong Heng Innovation Technology Co., Ltd., LC3000 (Ddlsogel, C18, 30 mm×250 mm 10 μm).

Thin layer chromatography (TLC) was performed with Huanghai HSGF 254 (5×20 cm) silica gel plates, and preparative thin layer chromatography was performed with GF 254 (0.4~0.5 nm) silica gel plates produced in Yantai.

The reaction was monitored by thin layer chromatography (TLC) or LC-MS, the developing solvent system included dichloromethane and methanol system, n-hexane and ethyl acetate system, as well as petroleum ether and ethyl acetate system, and was adjusted (by adjusting the volume ratio of the solvents, or by adding triethylamine, etc.) according to the polarity of the compound to be separated.

The microwave reaction was conducted by CEM Discovery Sp (400 W, RT~300° C.) microwave reactor.

Silica gel (200~300 mesh) produced by Yucheng Chemical Co., Ltd was normally employed as a stationary phase in column chromatography. The eluent system included dichloromethane and methanol system, as well as n-hexane and ethyl acetate system, and was adjusted (by adjusting the volume ratio of the solvents, or by adding triethylamine, etc.) according to the polarity of the compound to be separated.

In the following examples, unless otherwise specified, the reaction temperature was room temperature (20° C.~30° C.).

The reagents employed in the Examples were purchased from companies such as Aldrich Chemical Company, Shanghai Bide Pharmatech Co. Ltd., Beijing Greenchem Co. Ltd., Shanghai Shaoyuan Co. Ltd. or Ables Technology Co. Ltd. etc.

The abbreviations as used in the present application have the following meanings:

| Abbreviation | Meaning |
|---|---|
| $Boc_2O$ | di-tert-butyl dicarbonate |
| DCM | dichloromethane |
| DIEA/DIPEA | N,N-diisopropylethylamine |
| DMAP | 4-dimethylaminopyridine |
| DMF | N,N-dimethylformamide |
| EtOH | ethanol |
| $K_2CO_3$ | potassium carbonate |
| LC-MS | liquid chromatographic-mass spectrometry |
| NaH | sodium hydride |
| Pd/C | palladium/carbon |
| $Pd(PPh_3)_4$ | tetrakis(triphenylphosphine)palladium |
| RT | room temperature |
| SEM | 2-(trimethylsilyl)ethoxymethyl |
| SEM-Cl | 2-(trimethylsilyl)ethoxymethyl chloride |
| TEA | triethylamine |

Example 1

Preparation of 5-((5-isopropyl-2,3-dihydro-1H-pyrrolo[2,3-b]pyridin-4-yl)oxy)pyrimidin-2,4-diamine (C1)

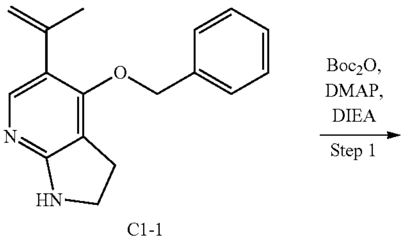

C1-1

-continued

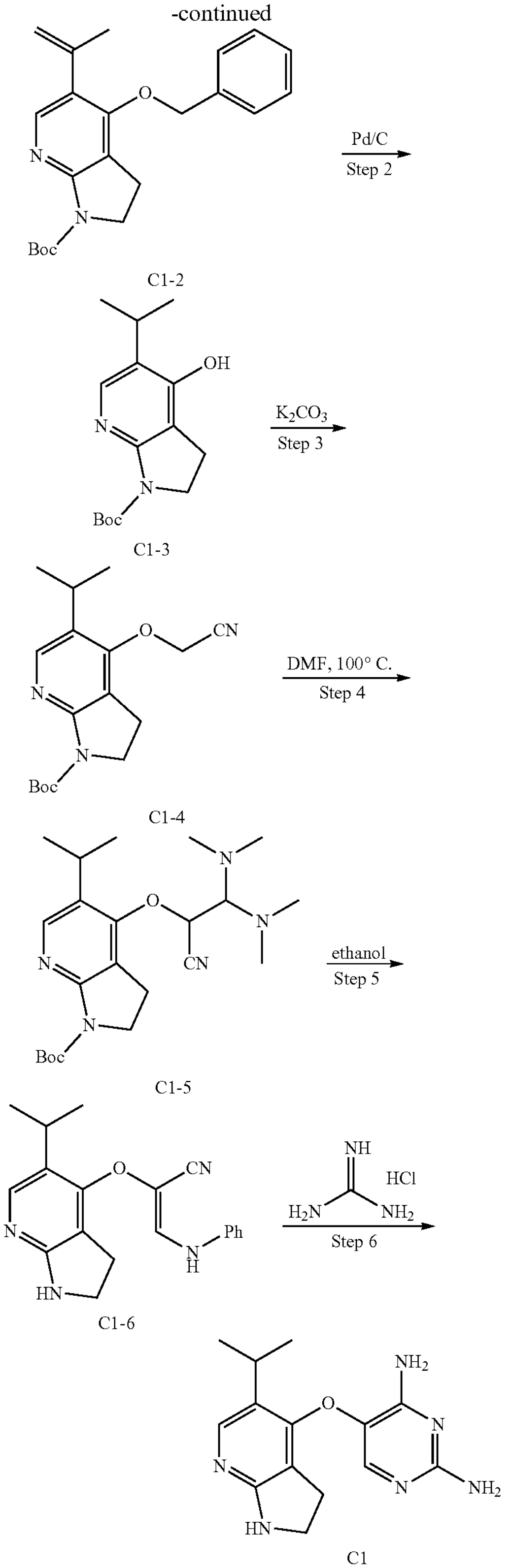

C1-2

C1-3

C1-4

C1-5

C1-6

C1

Step 1:

C1-1 (2 g, 7.57 mmol) was dissolved in dichloromethane (5 mL), and $Boc_2O$ (2.5 g, 11.4 mmol), DIEA (1.7 g, 13.2 mmol) and DMAP (0.8 g, 6.6 mmol) were sequentially added. The reaction solution was stirred at room temperature overnight. After LC-MS indicated the reaction was complete, the reaction was quenched by adding water, and extracted with ethyl acetate (50 mL*2). The organic phase was dried, concentrated, and the residue was separated and purified by column chromatography (petroleum ether:ethyl acetate=10:1) to afford compound C1-2 (1.5 g, yield 54.3%). MS m/z (ESI): 365.0 $[M+H]^+$.

Step 2:

C1-2 (1.5 g, 4.1 mmol) was dissolved in ethanol (15 mL), wet Pd/C (0.5 g) was added to the reaction solution, purge with hydrogen was performed for 3 times, and the reaction was allowed to proceed at room temperature for 2 hours. After LC-MS indicated the reaction was complete, palladium/carbon was filtered off, and the filtrate was concentrated to dryness to afford C1-3 (1.0 g, yield 87.7%), which was used directly in the next step. MS m/z (ESI): 278.9 $[M+H]^+$.

Step 3:

C1-3 (1 g, 3.6 mmol) was dissolved in DMF (10 mL), bromoacetonitrile (0.47 g, 3.96 mmol) and potassium carbonate (1 g, 7.2 mmol) were added to the reaction solution. The reaction solution was stirred at room temperature overnight. After LC-MS indicated the reaction was complete, the reaction was quenched by adding water, extracted with ethyl acetate, concentrated, and the residue was separated and purified by column chromatography (petroleum ether:ethyl acetate=1:1), to afford C1-4 (600 mg, yield 52.6%). MS m/z (ESI): 318.0 $[M+H]^+$.

Step 4:

C1-4 (600 mg, 1.89 mmol) was dissolved in DMF (5 mL), and tert-butoxy bis(dimethylamino)methane (0.99 g, 5.68 mmol) was added to the reaction solution. The reaction solution was stirred at 100° C. for 1 hour. After LC-MS indicated the reaction was complete, the reaction was quenched by adding water, extracted with ethyl acetate, and the organic phase was concentrated to afford C1-5 (700 mg, oil, yield 88.7%). MS m/z (ESI): 373.0 $[M-45+H]^+$.

Step 5:

C1-5 (700 mg, 1.67 mmol) was dissolved in ethanol (10 mL), and aniline hydrobromide (390 mg, 2.25 mmol) was added to the reaction solution. The reaction solution was stirred under reflux overnight. After LC-MS indicated the reaction was complete, the reaction was quenched by adding water. The reaction solution was concentrated, the residue was separated and purified by a Prep-TLC method (petroleum ether:ethyl acetate=1:1), to afford C1-6 (300 mg, yellow solid, yield 55.8%). MS m/z (ESI): 321.0 $[M+H]^+$.

Step 6:

C1-6 (150 mg, 0.47 mmol) was dissolved in ethanol (5 mL), and guanidine hydrochloride (134 mg, 1.41 mmol) and sodium methoxide (76 mg, 1.41 mmol) were added to the reaction solution. The reaction solution was stirred under reflux overnight. After LC-MS indicated the reaction was complete, the reaction solution was concentrated through rotary evaporation, and the residue was separated and purified by a Prep-HPLC method to afford C1 (31.5 mg, white solid, yield 23.5%).

$^1H$ NMR (400 MHz, MeOD) δ 7.76 (s, 1H), 7.47 (s, 1H), 3.86-3.82 (m, 2H), 3.19-3.16 (m, 1H), 2.98-2.94 (m, 2H), 1.30 (d, J=6.8 Hz, 6H). MS m/z (ESI): 286.9 $[M+H]^+$.

Example 2

Preparation of 5-((5-isopropyl-1H-pyrrolo[2,3-b]pyridin-4-yl)oxy)pyrimidin-2,4-diamine (C4) and 5-((5-isopropyl-1-((2-(trimethylsilyl)ethoxy)methyl)-1H-pyrrolo[2,3-b]pyridin-4-yl)oxy)pyrimidin-2,4-diamine (C9)

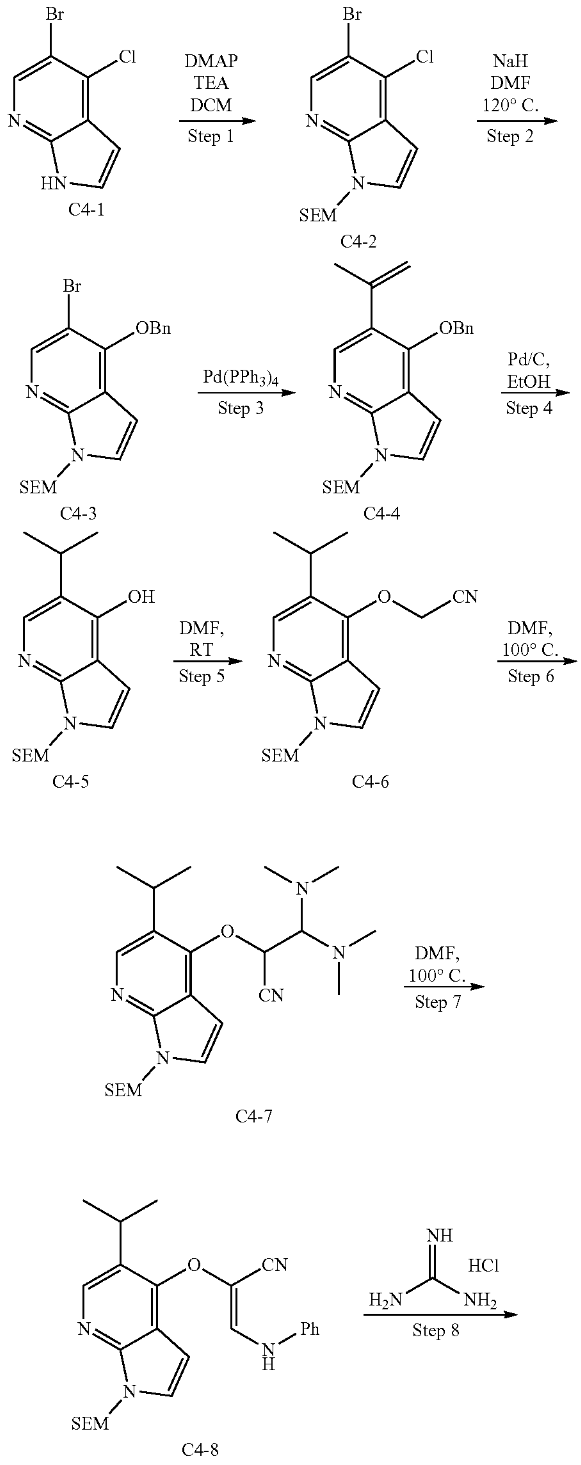

-continued

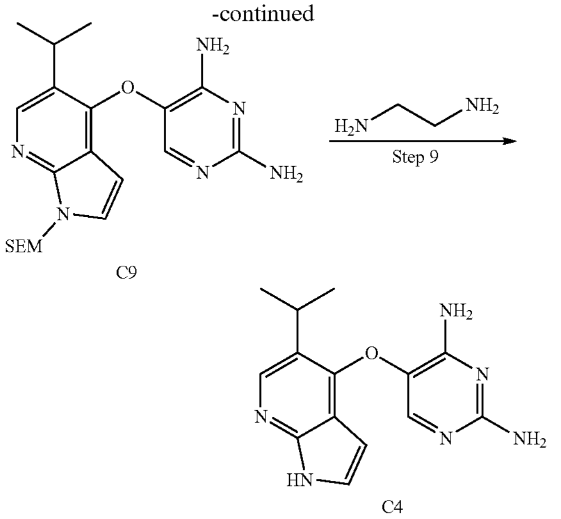

C9

C4

Step 1:

C4-1 (7.0 g, 30 mmol) was dissolved in DMF (20 mL), sodium hydride (0.2 g, 8.6 mmol) was added to the reaction solution at 0° C., and the reaction was stirred for 10 minutes. SEM-Cl (6.1 g, 36 mmol) was then dropwise added to the reaction solution, and the reaction was stirred at room temperature for 1 hour. After LC-MS indicated the reaction was complete, the reaction was quenched by adding water (5 mL), and extracted with ethyl acetate (30 mL*3). The organic phase was concentrated, the residue was separated and purified by column chromatography (petroleum ether: ethyl acetate=10:1), to afford C4-2 (3.5 g, oil, yield 32.2%). MS m/z (ESI): 360.8 $[M+H]^+$.

Step 2:

C4-2 (3.5 g, 9.7 mmol) was dissolved in DMF (10 mL), benzyl alcohol (1.6 g, 14.6 mmol) and sodium hydride (0.465 g, 19.4 mmol) were added to the reaction solution at 0° C. The reaction solution was stirred at room temperature for 1 hour. After LC-MS indicated the reaction was complete, the reaction was quenched by adding water (20 mL), and extracted with ethyl acetate (20 mL*3). The organic phase was concentrated, the residue was separated and purified by column chromatography (petroleum ether:ethyl acetate=5:1), to afford C4-3 (1 g, oil, yield 24.4%). MS m/z (ESI): 432.8 $[M+H]^+$.

Step 3:

C4-3 (0.1 g, 0.23 mmol) was dissolved in 1,4-dioxane (10 mL), isopropenyl pinacol borate (70 mg, 0.42 mmol), potassium carbonate (77.4 mg, 0.56 mmol) and tetrakis(triphenylphosphine)palladium (10 mg) were added to the reaction solution, purge with nitrogen was performed for three times, and the reaction was allowed to proceed at 90° C. overnight. After LC-MS indicated the reaction was complete, the reaction was quenched by adding water (1 mL), and extracted with ethyl acetate (10 mL*3). The organic phase was concentrated, the residue was separated and purified by column chromatography (petroleum ether:ethyl acetate=10:1), to afford C4-4 (0.1 g, oil, yield 100%). MS m/z (ESI): 394.9 $[M+H]^+$.

Step 4:

C4-4 (100 mg, 0.254 mmol) was dissolved in ethanol (5 mL), Pd/C (10 mg) was added to the reaction solution, purge with hydrogen was performed for three times, and the reaction was allowed to proceed at room temperature for 2 hours. After LC-MS indicated the reaction was complete, palladium/carbon was filtered off, the filtrate was concentrated to dryness to afford C4-5 (0.1 g crude product, 100%), which was used directly in the next step. MS m/z (ESI): 307.0 $[M+H]^+$.

Step 5:

C4-5 (0.1 g crude product, 0.32 mmol) was dissolved in DMF (2 mL), bromoacetonitrile (47 mg, 0.39 mmol) and potassium carbonate (90 mg, 0.64 mmol) were added to the reaction solution. The reaction solution was stirred at room temperature overnight. After LC-MS indicated the reaction was complete, the reaction was quenched by adding water (1 mL), and extracted with ethyl acetate. The organic phase was concentrated, the residue was separated and purified by column chromatography (petroleum ether:ethyl acetate=5:1), to afford C4-6 (60 mg, yield 53.1%). MS m/z (ESI): 345.9 $[M+H]^+$.

Step 6:

C4-6 (60 mg, 0.17 mmol) was dissolved in DMF (2 mL), and tert-butoxy bis(dimethylamino)methane (0.1 mg, 0.57 mmol) was added to the reaction solution. The reaction solution was stirred at 100° C. for 1 hour. After LC-MS indicated the reaction was complete, the reaction was quenched by adding water (1 mL), and extracted with ethyl acetate (10 mL*3). The organic phase was concentrated, the residue was separated and purified by a Prep-TLC method (petroleum ether:ethyl acetate=2:1), to afford C4-7 (30 mg, yield 38.7%). MS m/z (ESI): 400.9 $[M-45+H]^+$.

Step 7:

C4-7 (20 mg, 0.049 mmol) was dissolved in ethanol (10 mL), and aniline hydrobromide (16.2 mg, 0.094 mmol) was added to the reaction solution. The reaction solution was stirred under reflux overnight. After LC-MS indicated the reaction was complete, the reaction was quenched by adding water (1 mL), and extracted with ethyl acetate (10 mL*3). The organic phase was concentrated, the residue was separated and purified by a Prep-TLC method (petroleum ether: ethyl acetate=1:2), to afford compound C4-8 (20 mg, yield 91.8%). MS m/z (ESI): 448.8 $[M+H]^+$.

Step 8:

C4-8 (20 mg, 0.048 mmol) was dissolved in ethanol (10 mL), guanidine hydrochloride (13.6 mg, 0.143 mmol) and sodium methoxide (7.7 mg, 0.143 mmol) were added to the reaction solution. The reaction solution was stirred under reflux overnight. After LC-MS indicated the reaction was complete, the reaction was concentrated through rotary evaporation, and the residue was separated and purified by a Prep-TLC method (ethyl acetate), to afford C9 (8 mg, yield 43.3%).

$^1H$ NMR (400 MHz, MeOD) δ 8.21 (s, 1H), 7.32 (d, J=3.6 Hz, 1H), 7.27 (s, 1H), 5.92 (d, J=3.6 Hz, 1H), 5.62 (s, 2H), 3.56-3.48 (m, 3H), 1.41 (d, J=7.2 Hz, 6H), 0.88-0.84 (m, 2H), 0.06 (s, 9H). MS m/z (ESI): 414.8 $[M+H]^+$.

Step 9:

C9 (6 mg, 0.014 mmol) was dissolved in DMF (1 mL), tetrabutylammonium fluoride (0.1 mL) and ethylenediamine (0.1 mL) were added to the reaction solution. The reaction solution was stirred at 80° C. for 1 hour. After LC-MS indicated the reaction was complete, The reaction solution was concentrated through rotary evaporation, and the residue was separated and purified by a Prep-HPLC method, to afford C4 (2 mg, yield 50.3%).

$^1H$ NMR (400 MHz, MeOD) δ 8.17 (s, 1H), 7.26 (s, 1H), 7.19 (s, 1H), 5.96 (s, 1H), 3.48-3.45 (m, 1H), 1.40 (d, J=6.8 Hz, 6H). MS m/z (ESI): 285.1 $[M+H]^+$.

The following compounds were prepared according to methods similar to those described in the above Examples.

| No. | Structural Formula |
|---|---|
| C2 | 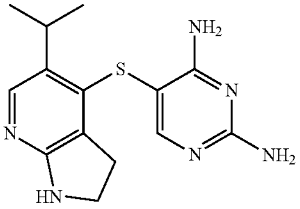 [SMILES: CC(C)c1cnc2c(c1Sc1cnc(N)nc1N)CCN2] |
| C3 | 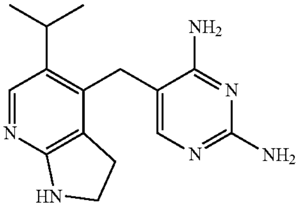 [SMILES: CC(C)c1cnc2c(c1Cc1cnc(N)nc1N)CCN2] |
| C5 | 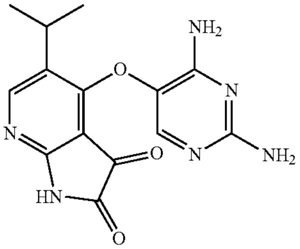 [SMILES: CC(C)c1cnc2c(c1Oc1cnc(N)nc1N)C(=O)C(=O)N2] |
| C6 | 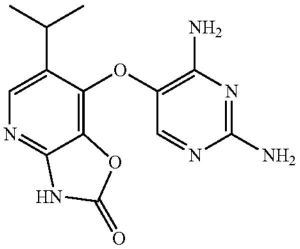 |
| C7 | 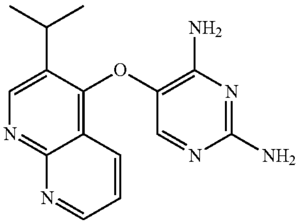 [SMILES: CC(C)c1cnc2ncccc2c1Oc1cnc(N)nc1N] |
| C8 | 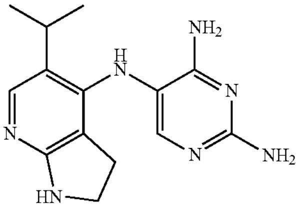 [SMILES: CC(C)c1cnc2c(c1Nc1cnc(N)nc1N)CCN2] |
-continued
| No. | Structural Formula |
|---|---|
| C10 | 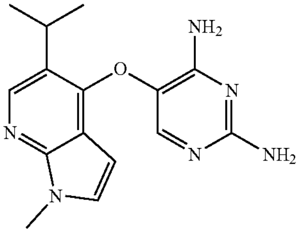 [SMILES: CC(C)c1cnc2c(ccn2C)c1Oc1cnc(N)nc1N] |
| C11 | 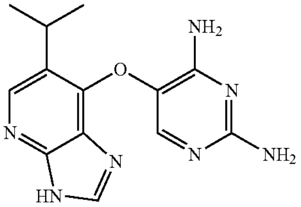 [SMILES: CC(C)c1cnc2[nH]cnc2c1Oc1cnc(N)nc1N] |
| C12 | 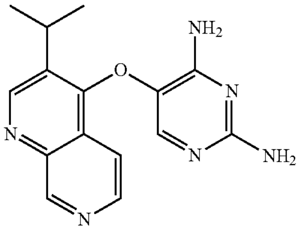 [SMILES: CC(C)c1cnc2cnccc2c1Oc1cnc(N)nc1N] |
| C13 | 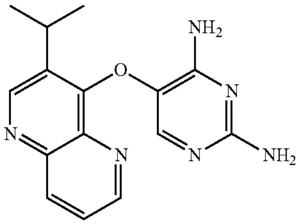 [SMILES: CC(C)c1cnc2cccnc2c1Oc1cnc(N)nc1N] |
| C14 | 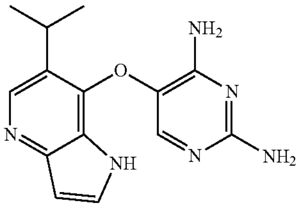 [SMILES: CC(C)c1cnc2cc[nH]c2c1Oc1cnc(N)nc1N] |
| C15 | 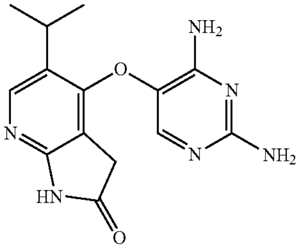 [SMILES: CC(C)c1cnc2c(c1Oc1cnc(N)nc1N)CC(=O)N2] |

-continued

| No. | Structural Formula |
|---|---|
| C16 | 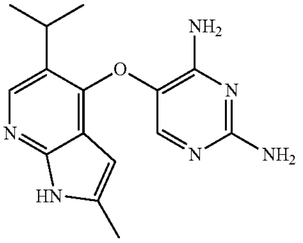 [SMILES: Cc1cc2c(Oc3cnc(N)nc3N)c(C(C)C)cnc2[nH]1] |
| C17 | 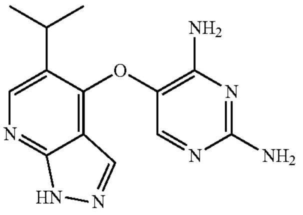 [SMILES: CC(C)c1cnc2[nH]ncc2c1Oc1cnc(N)nc1N] |
| C18 | 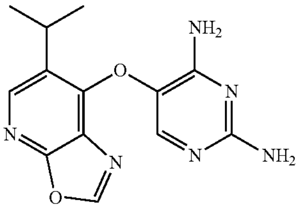 [SMILES: CC(C)c1cnc2ocnc2c1Oc1cnc(N)nc1N] |
| C19 | 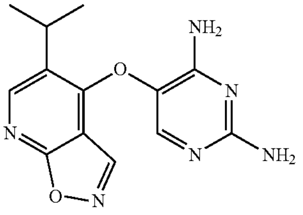 [SMILES: CC(C)c1cnc2oncc2c1Oc1cnc(N)nc1N] |
| C20 | 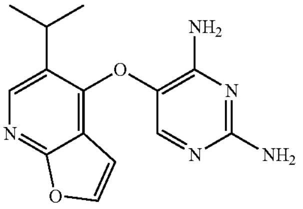 [SMILES: CC(C)c1cnc2occc2c1Oc1cnc(N)nc1N] |
| C21 | 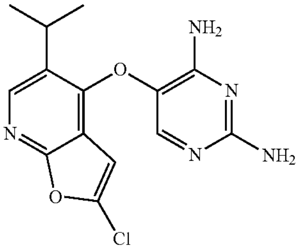 [SMILES: CC(C)c1cnc2oc(Cl)cc2c1Oc1cnc(N)nc1N] |
| C22 | 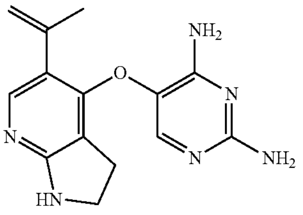 [SMILES: C=C(C)c1cnc2c(c1Oc1cnc(N)nc1N)CCN2] |

-continued

| No. | Structural Formula |
|---|---|
| C23 | 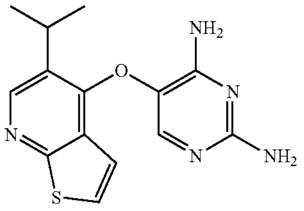 |
| C24 | 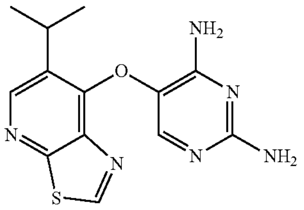 |

Biological Assay: Determination of the Inhibitory Activity of the Compounds on Human P2X3 and P2X2/3 Receptors Cells were seeded into a poly-D-lysine-coated 384-well cell culture plate (Corning) at a density of 11,000 cells/well/25 μL of cell inoculation medium, and were cultured in a cell incubator overnight. On the day of the test, the calcium 6 dye was diluted to a 2× concentration with an assay buffer, 25 μL of the 2× calcium 6 dye was added to the 384-well cell culture plate, which was incubated at 37° C. for 2 hours, and then placed at room temperature for further use. The test compound and the agonist, α,β-MeATP were diluted to a 7× concentration with the assay buffer, 10 μL of the 7× test compound was added to the 384-well cell culture plate, which was incubated at room temperature for 15 minutes, and 10 μL of the 7× α,β-MeATP was transferred into the 384-well cell culture plate. The data were measured and analyzed using FLIPR Tetra, and the half inhibitory concentration ($IC_{50}$) of the test compound on P2X3 and P2X2/3 receptors was calculated with the GraphPad Prism four-parameter equation.

- Cell lines: human embryonic kidney cells HEK293-P2X3 and HEK293-P2X2/3 stably expressing cell lines;
- Complete cell culture medium: DMEM High Glucose (Life Technology), which contained 10% fetal bovine serum, 4 mM GlutaMAX, 1% penicillin-streptomycin, and 350 μg/mL G418;
- Cell inoculation medium: DMEM High Glucose (Life Technology), which contained 2% fetal bovine serum, and 4 mM GlutaMAX;
- Cell culture conditions: 37° C., 5% $CO_2$;
- Assay buffer: HBSS (containing calcium and magnesium ions), which contained 20 mM HEPES;
- Detection equipment: FLIPR Tetra (Molecular Devices);
- Detection parameters: excitation wavelength 470-495 nm, emission wavelength 515-575 nm; fluorescence signal was measured once every second for 260 seconds in total.

The experimental data obtained from the above biological assay are shown in the table below.

| Compound No. | P2X3 $IC_{50}$ (μM) | P2X2/3 $IC_{50}$ (μM) |
|---|---|---|
| C1 | 0.0605 | 0.1004 |
| C4 | 0.086 | 0.080 |

Various modifications of the invention in addition to those described herein will become apparent to those skilled in the art from the foregoing description. Such modifications are intended to fall within the scope of the appended claims Each reference, including all patents, applications, journal articles, books and any other disclosure, referred to herein is hereby incorporated by reference in its entirety.

What is claimed is:

1. A compound, or a pharmaceutically acceptable salt, ester, stereoisomer, polymorph, solvate, N-oxide, or isotopically labeled compound thereof, wherein the compound has the structure of any of the following formulae:

(V-1)

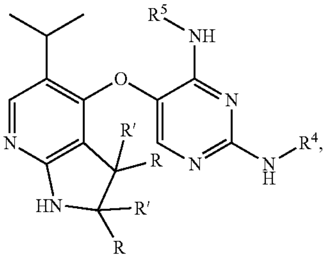

(V-2)

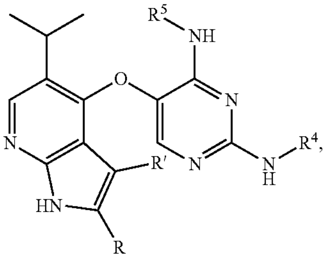

(V-3)

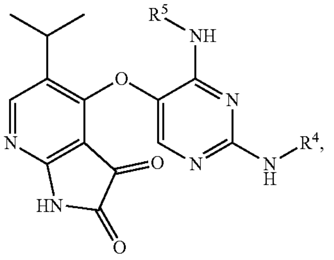

(V-4)

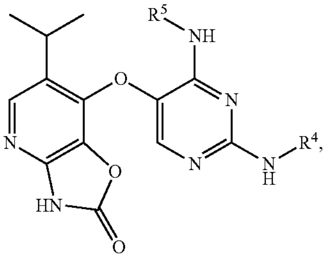

(V-5)

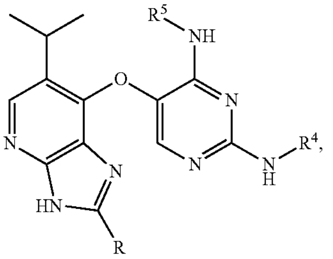

-continued (V-6)

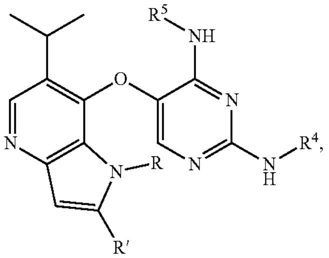

(V-7)

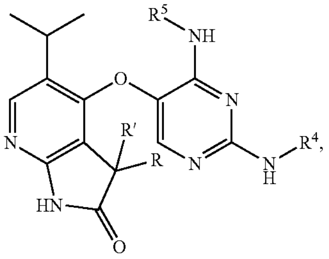

(V-8)

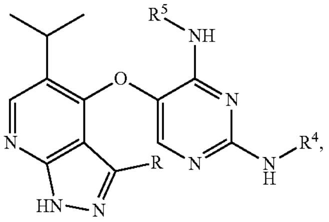

(V-9)

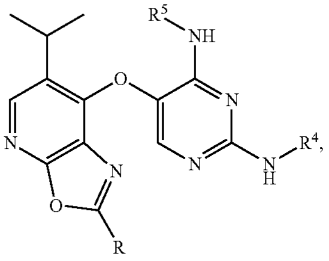

(V-10)

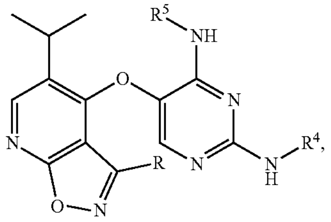

(V-11)

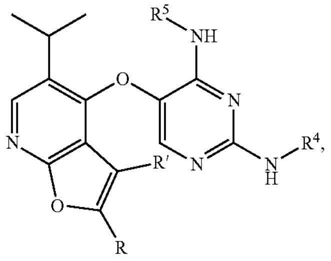

-continued (V-12)

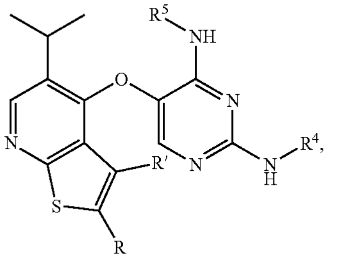

(V-13)

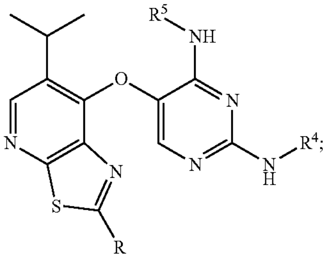

$R^4$ and $R^5$ are each independently selected from the group consisting of H, —C(=O)OR$^a$, —NR$^a$R$^b$, —NR$^a$—C(=O)R$^b$, —NR$^a$—C(=O)OR$^b$, —$C_{1-6}$ alkylene-NR$^a$R$^b$, —$C_{1-6}$ alkylene-OR$^a$, —$C_{1-6}$ alkylene-O—$C_{1-6}$ alkylene-OR$^a$, $C_{1-6}$ alkyl, $C_{1-6}$ haloalkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl and $C_{6-12}$ aralkyl;

the above alkyl, alkylene, alkenyl, alkynyl, cyclic hydrocarbyl, heterocyclyl, aryl, heteroaryl and aralkyl, at each occurrence, are each optionally substituted with one or more substituents independently selected from the group consisting of: halogen, hydroxyl, oxo, amino, cyano, nitro, —Si(R)$_3$, $C_{1-6}$ alkyl, saturated or partially unsaturated $C_{3-6}$ cyclic hydrocarbyl, saturated or partially unsaturated 3-10-membered heterocyclyl, $C_{6-10}$ aryl, 5-14-membered heteroaryl, $C_{6-12}$ aralkyl, —C(=O)R$^a$, —OC(=O)R$^a$, —C(=O)OR$^a$, —OR$^a$, —SR$^a$, —S(=O)R$^a$, —S(=O)$_2$R$^a$, —S(=O)$_2$NR$^a$R$^b$, —NR$^a$R$^b$, —C(=O)NR$^a$R$^b$, —NR$^a$—C(=O)R$^b$, —NR$^a$—C(=O)OR$^b$, —NR$^a$—S(=O)$_2$—R$^b$, —NR$^a$—C(=O)—NR$^a$R$^b$, —$C_{1-6}$ alkylene-NR$^a$R$^b$, —$C_{1-6}$ alkylene-OR$^a$, —$C_{1-6}$ alkenylene-OR$^a$ and —O—$C_{1-6}$ alkylene-NR$^a$R$^b$, the alkyl, cyclic hydrocarbyl, heterocyclyl, aryl, heteroaryl and aralkyl are further optionally substituted with one or more substituents independently selected from the group consisting of: halogen, hydroxyl, oxo, amino, cyano, nitro, —NR$^a$R$^b$, $C_{1-6}$ alkyl, —O—$C_{1-6}$ alkyl, saturated or partially unsaturated $C_{3-6}$ cyclic hydrocarbyl, saturated or partially unsaturated 3-10-membered heterocyclyl, $C_{6-10}$ aryl, 5-14-membered heteroaryl and $C_{6-12}$ aralkyl;

R$^a$ and R$^b$, at each occurrence, are each independently selected from the group consisting of H, —OH, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl and $C_{6-12}$ aralkyl; alternatively, R$^a$ and R$^b$ together with the atom to which they are attached form a 3-12-membered heterocycle or heteroaromatic ring, and the above groups are further optionally substituted with one or more substituents independently selected from the group consisting of: halogen, hydroxyl, oxo, amino, cyano, nitro, $C_{1-6}$ alkyl, —O—$C_{1-6}$ alkyl, saturated or partially unsaturated $C_{3-6}$ cyclic hydrocarbyl, saturated or partially unsaturated 3-10-membered heterocyclyl, $C_{6-10}$ aryl, 5-14-membered heteroaryl and $C_{6-12}$ aralkyl; and R and R', at each occurrence, are each independently selected from the group consisting of H, SEM, halogen, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3-10-membered heterocyclyl, $C_{6-10}$ aryl, 5-14-membered heteroaryl and $C_{6-12}$ aralkyl, and at most 2 ring members in the cyclic hydrocarbyl and heterocyclyl are C(=O).

2. The compound according to claim 1, or a pharmaceutically acceptable salt, ester, stereoisomer, polymorph, solvate, N-oxide, or isotopically labeled compound thereof, wherein R$^a$ and R$^b$, at each occurrence, are each independently selected from the group consisting of H, —OH, methyl, ethyl, n-propyl, isopropyl, cyclopropyl, phenyl, and benzyl, and; alternatively, R$^a$ and R$^b$ together with the atom to which they are attached form a 5-8-membered heterocycle or heteroaromatic ring.

3. The compound according to claim 1, or a pharmaceutically acceptable salt, ester, stereoisomer, polymorph, solvate, N-oxide, or isotopically labeled compound thereof, wherein $R^4$ and $R^5$ are each independently selected from the group consisting of H, —C(=O)OC(CH$_3$)$_3$, —NH$_2$, —NHCH$_3$, —NHPh, —NHC(=O)CH$_3$, —NHBoc, methyl, ethyl, —CH$_2$CF$_3$, n-propyl, isopropyl, n-butyl, isobutyl, tert-butyl, cyclopropyl, cyclobutyl, cyclopentyl, cyclohexyl, phenyl, benzyl,

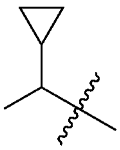,
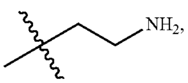
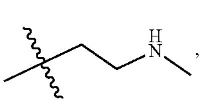
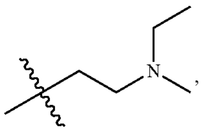
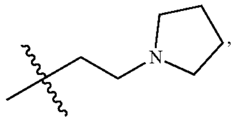
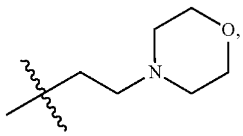
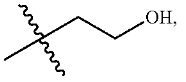
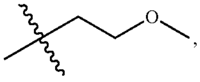
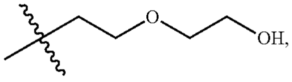
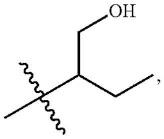,
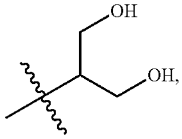
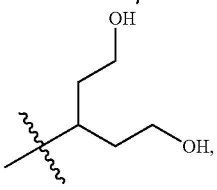
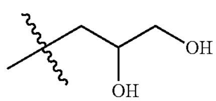
and -continued
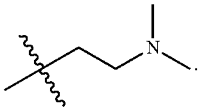
4. The compound according to claim 1, or a pharmaceutically acceptable salt, ester, stereoisomer, polymorph, solvate, N-oxide, or isotopically labeled compound thereof, wherein the compound has the following structure:
C1
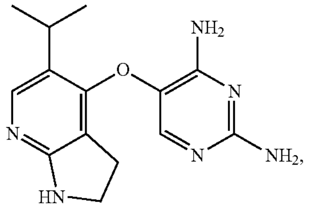
C4
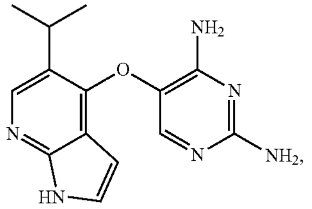
C5
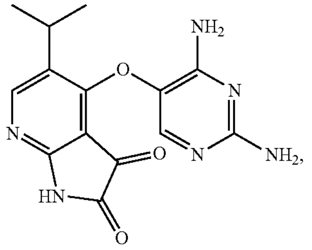
C6
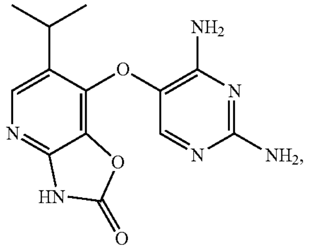
C9
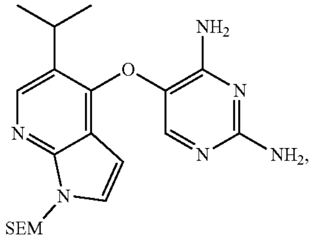
-continued
C10
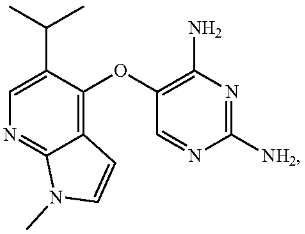
C11
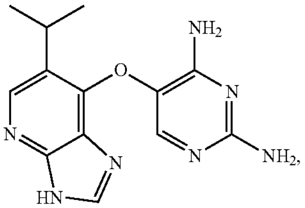
C14
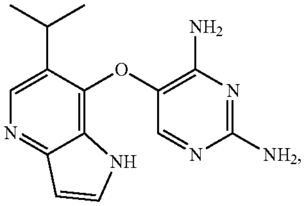
C15
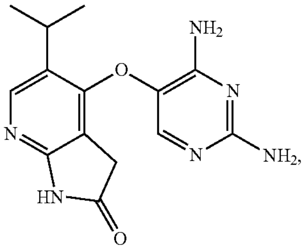
C16
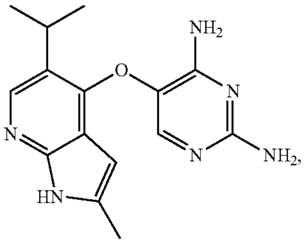
C17
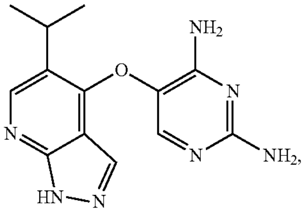
C18
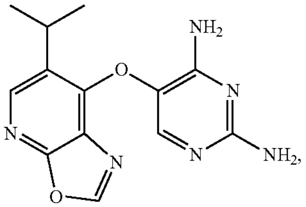

-continued

C19

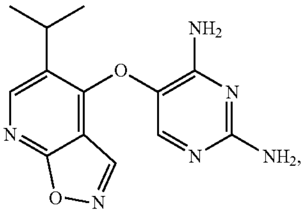

C20

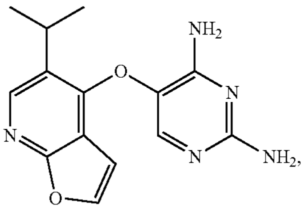

C21

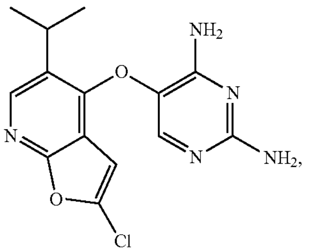

-continued

C23

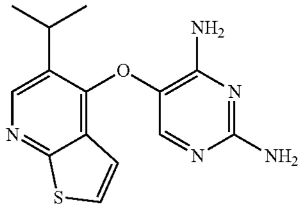 [SMILES: CC(C)c1cnc2sccc2c1Oc1cnc(N)nc1N]

or

C24

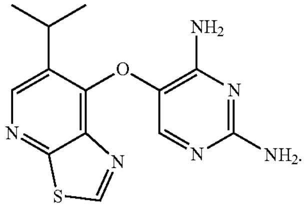

5. A pharmaceutical composition comprising a therapeutically effective amount of the compound according to claim 1, or a pharmaceutically acceptable salt, ester, stereoisomer, polymorph, solvate, N-oxide, or isotopically labeled compound thereof, and a pharmaceutically acceptable carrier.

6. The pharmaceutical composition according to claim 5, which is in the form of a solid, semi-solid, liquid, or gas preparation.

* * * * *